(12) United States Patent
Nelson et al.

(10) Patent No.: US 10,870,845 B2
(45) Date of Patent: Dec. 22, 2020

(54) METHODS FOR CAPTURING NUCLEIC ACIDS

(71) Applicant: Global Life Sciences Solutions Operations UK Ltd, Sheffield (GB)

(72) Inventors: John Richard Nelson, Clifton Park, NY (US); Bing Li, Clifton Park, NY (US)

(73) Assignee: Global Life Sciences Solutions Operations UK Ltd, Sheffield (GB)

(*) Notice: Subject to any disclaimer, the term of this patent is extended or adjusted under 35 U.S.C. 154(b) by 152 days.

(21) Appl. No.: 14/566,865

(22) Filed: Dec. 11, 2014

(65) Prior Publication Data

US 2016/0002622 A1   Jan. 7, 2016

Related U.S. Application Data

(63) Continuation-in-part of application No. 14/321,160, filed on Jul. 1, 2014, now Pat. No. 10,472,620.

(51) Int. Cl.
*C12Q 1/68* (2018.01)
*C12N 15/10* (2006.01)

(52) U.S. Cl.
CPC ................. *C12N 15/1006* (2013.01)

(58) Field of Classification Search
USPC ............ 435/6.1, 6.11, 6.12, 91.1, 91.2, 183, 435/287.1, 287.2; 436/94, 501; 536/23.1, 24.3, 24.33, 25.3; 422/50, 68.1
See application file for complete search history.

(56) References Cited

U.S. PATENT DOCUMENTS

| | | | |
|---|---|---|---|
| 5,955,351 A | 9/1999 | Gerdes et al. | |
| 6,037,127 A | 3/2000 | Ebersole et al. | |
| 6,221,603 B1 | 4/2001 | Mahtani | |
| 6,255,082 B1* | 7/2001 | Lizardi ................ | C12Q 1/6844 435/5 |
| 6,608,186 B1 | 8/2003 | Miculka et al. | |
| 7,153,955 B2 | 12/2006 | Miculka et al. | |
| 7,358,047 B2 | 4/2008 | Hafner et al. | |
| 7,589,187 B2 | 9/2009 | McCall et al. | |
| 7,618,776 B2 | 11/2009 | Lizardi | |
| 7,858,396 B2* | 12/2010 | Corstjens ......... | G01N 33/54386 422/423 |
| 8,003,407 B2 | 8/2011 | Zhou et al. | |
| 8,043,811 B2 | 10/2011 | Danks et al. | |
| 8,062,850 B2 | 11/2011 | Piepenburg et al. | |
| 9,745,616 B2 | 8/2017 | Terbrueggen et al. | |
| 2002/0172973 A1* | 11/2002 | Hosoi .................. | B01J 19/0046 435/6.11 |
| 2003/0032024 A1 | 2/2003 | Lizardi | |
| 2003/0087271 A1 | 5/2003 | Ebersole et al. | |
| 2003/0190608 A1 | 10/2003 | Blackburn | |
| 2004/0110167 A1 | 6/2004 | Gerdes et al. | |
| 2005/0112636 A1 | 5/2005 | Hurt et al. | |
| 2005/0227275 A1 | 10/2005 | Jung et al. | |
| 2006/0160078 A1 | 7/2006 | Cardy et al. | |
| 2007/0104962 A1 | 5/2007 | Laas et al. | |
| 2009/0047673 A1 | 2/2009 | Cary | |
| 2009/0136924 A1* | 5/2009 | Larionov ............... | C12N 15/85 435/6.11 |
| 2009/0143570 A1 | 6/2009 | Jiang et al. | |
| 2009/0148933 A1 | 6/2009 | Battrell et al. | |
| 2009/0186344 A1 | 7/2009 | Farinas | |
| 2010/0190179 A1 | 7/2010 | Nilsen | |
| 2011/0117540 A1 | 5/2011 | Cary | |
| 2011/0171652 A1 | 7/2011 | You | |
| 2011/0220502 A1 | 9/2011 | Selden et al. | |
| 2011/0244467 A1 | 10/2011 | Haswell | |
| 2011/0287951 A1 | 11/2011 | Emmert-Buck et al. | |
| 2011/0294167 A1 | 12/2011 | McEwan et al. | |
| 2012/0015358 A1 | 1/2012 | Scarr et al. | |
| 2013/0210025 A1 | 8/2013 | Babu et al. | |

(Continued)

FOREIGN PATENT DOCUMENTS

CN    101473043 A    7/2009
EP    2369015 A1    9/2011

(Continued)

OTHER PUBLICATIONS

Rohrman et al., A Lateral Flow Assay for Quantitative Detection of Amplified HIV-1 RNA. PLOS ONE, 7, e45611, Sep. 2012.*
"Rolling circle amplification" from Wikipedia. Printed on Aug. 31, 2020.*
International Search Report and Written Opinion issued in connection with corresponding PCT Application No. PCT/US15/63468 dated Feb. 25, 2016.
Brown T., "Curr Protoc Immunol", May 2001; Chapter 10:Unit 10.6A. doi: 10.1002/0471142735.im1006as06, Abstract—1Page.
Cannon G, Heinhorst S, Weissbach A, "Quantitative molecular hybridization on nylon membranes". Aug. 15, 1985;149(1), Abstract—1 page.
Twomey TA1, Krawetz SA, "Parameters affecting hybridization of nucleic acids blotted onto nylon or nitrocellulose membranes". Biotechniques May 1990; 8(5), Abstract—1 page.

(Continued)

Primary Examiner — Frank W Lu
(74) Attorney, Agent, or Firm — Eversheds Sutherland (US) LLP

(57) ABSTRACT

A method is provided herein, wherein the method of capturing a target nucleic acid, comprises applying a nucleic acid capture probe to a capture zone of a needs definition, wherein the nucleic acid capture probe having a first molecular weight comprises at least a sequence that is complimentary to at least a portion of the target nucleic acid sequence and the nucleic acid capture probe is substantially immobilized at the capture zone of the substrate. The method further comprises applying a sample comprising the target nucleic acid having a second molecular weight to a sample application zone of the substrate; wherein the sample comprising the target nucleic acid flows across a length of the substrate from the sample application zone to the capture zone by lateral flow, and the target nucleic acid is captured by the nucleic acid capture probes by hybridization to the capture zone.

26 Claims, 8 Drawing Sheets
Specification includes a Sequence Listing.

(56) References Cited

U.S. PATENT DOCUMENTS

| | | |
|---|---|---|
| 2013/0230846 A1 | 9/2013 | Babu et al. |
| 2013/0295583 A1 | 11/2013 | Babu et al. |
| 2014/0039177 A1 | 2/2014 | Nelson et al. |
| 2014/0093878 A1 | 4/2014 | Nelson et al. |
| 2014/0113839 A1 | 4/2014 | Wu et al. |
| 2014/0162244 A1 | 6/2014 | Bau et al. |
| 2014/0272939 A1 | 9/2014 | Aghvanyan et al. |

FOREIGN PATENT DOCUMENTS

| | | |
|---|---|---|
| WO | 1999009216 A2 | 2/1999 |
| WO | 2003066817 A2 | 8/2003 |
| WO | 2004007078 A1 | 1/2004 |
| WO | 2006041524 A2 | 4/2006 |
| WO | 2006074162 A2 | 7/2006 |
| WO | 2007092538 A2 | 8/2007 |
| WO | 2009034181 A2 | 3/2009 |
| WO | 2013067272 A1 | 5/2013 |

OTHER PUBLICATIONS

PCT Search Report and Written Opinion from PCT Application No. PCT/US2015/038028 dated Oct. 28, 2015.
PCT Search Report and Written Opinion from PCT Application No. PCT/US2015/036981 dated Nov. 24, 2015.
Rohrman et al., "A Lateral Flow Assay for Quantitative Detection of Amplified Hiv-1 Rna", PLOS One, vol. 7, No. 9, Sep. 2012, 8 pages.
Nelson et al., filed Jul. 1, 2014, U.S. Appl. No. 14/321,235.
Nelson et al., filed Jul. 1, 2014, U.S. Appl. No. 14/321,160.
Baner et al., "Signal amplification of padlock probes by rolling circle replication", Oxford journal, Nucleic acid research, vol. 26, Issue 22, pp. 5073-5078, Oct. 1998.
Thomas et al., "Amplification of Padlock Probes for DNA Diagnostics by Cascade Rolling Circle Amplification or the Polymerase Chain Reaction", Archives of pathology and laboratory medicine, vol. 123, Issue 12, pp. 1170-1176, Dec. 1999.
Mongkol Pongsuchart et al., "Sensitivity enhancement of nucleic acid detection by lateral flow strip test using UV crosslink method", Asian Biomedicine vol. 6 No. 3 Jun. 2012; 459-463.
"Guanidinium thiccyanate" from Wikipedia, the free encyclopedia. Printed on Apr. 13, 2017.
Sebastian Kersting et al."Rapid detection of Plasmodium falciparum with isothermal recombinase polymerase amplification and lateral flow analysis"; Licensee BioMed Central Ltd. 2014; Published: Mar. 15, 2014; Abstract—1page.
European Search Report issued in connection with corresponding EP application No. 15868310.2 dated Jun. 6, 2018.
European Search Report issued in connection with corresponding EP application No. 15814648.0 dated Jan. 11, 2018.
Hingxing Liu et. al. "Visual and sensitive detection of viable pathogenic bacteria by sensing of RNA markers in gold nanoparticles based paper platform" Biosensors and Bioelectronics, vol. 62, Jun. 14, 2014, pp. 38-46, XP055435634, ISSN: 0956-5663.
Chinese Office Action for CN Application No. 201580067328.8 dated Jun. 5, 2020 (26 pages with English translation).
Long et al., "An Isothermal and Sensitive Nucleic Acids Assay by Target Sequence Recycled Rolling Circle Amplification," Biosensors and Bioelectronics, 2013, 46:102-107.

\* cited by examiner

At room temp.

At 50°C

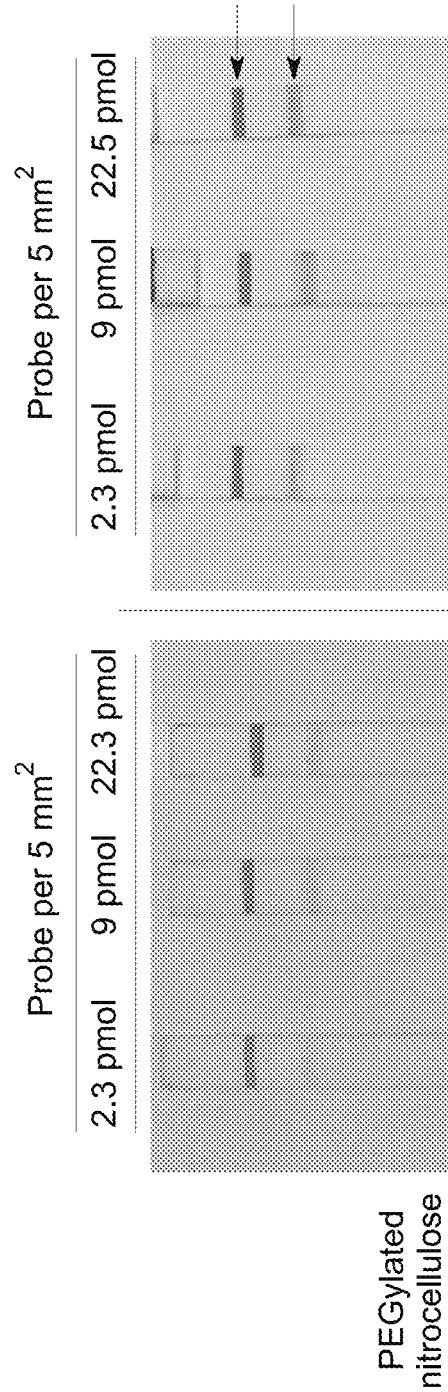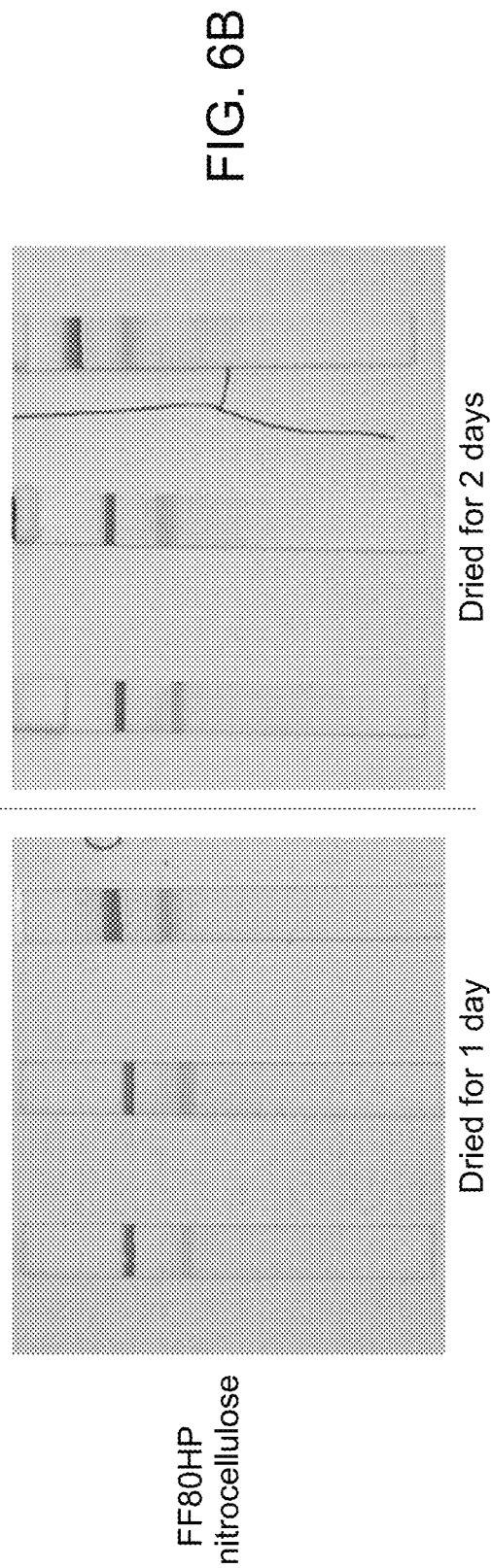

METHODS FOR CAPTURING NUCLEIC ACIDS

CROSS REFERENCE TO RELATED APPLICATIONS

This application is a continuation-in-part of U.S. patent application Ser. No. 14/321,160, entitled "Method, Substrate and Device for Separating Nucleic Acid", filed Jul. 1, 2014, now U.S. Pat. No. 10,472,620 B2; which is herein incorporated by reference.

SEQUENCE LISTING

The instant application contains a Sequence Listing which has been submitted electronically in ASCII format and is hereby incorporated by reference in its entirety. Said ASCII copy, created on Jan. 16, 2015, is named 276652-1_SL.txt and is 2,582 bytes in size.

This invention was made with Government support under grant number HR0011-11-2-0007 awarded by the Defense Advanced Research Projects Agency (DARPA). The Government has certain rights in the invention.

FIELD

The invention generally relates to methods for separating target nucleic acids from a biological sample. The invention also relates to methods of capturing target nucleic acids using nucleic acid capture probes by lateral flow.

BACKGROUND

Separation, detection, and concentration of nucleic acids from a sample are primary requirements for a variety of applications, such as basic research, forensic and diagnostic applications, sensing, genome sequencing, and the like. Various applications involving nucleic acids are typically preceded by separation and purification of target nucleic acids from unwanted nucleic acids and contaminants to reduce interference in downstream applications and to achieve desired result. Techniques including gel electrophoresis, capillary electrophoresis or electrophoresis in microfluidic or microanalytical devices, which are mainstay in molecular and cell biology enabling separation and purification of specific nucleic acids. The traditional purification or separation methods and the associated techniques are time consuming and labor intensive.

Detection of nucleic acids is of utmost importance in multiple applications, including but are not limited to, diagnostic applications, forensic analysis, genome sequencing, clinical studies and biopharmaceutical research. Various detection probes are currently being used to determine gene expression in normal and/or abnormal conditions, genomic screening for predicting a number of genetic disorders, to detect presence of mutant genes such as oncogenes in an individual, or to identify presence of infectious organisms such as bacteria and viruses. However, the lack of specificity, selectivity and resolution remain significant obstacles in currently used nucleic acid detection systems. To achieve desired concentration of target nucleic acids or detection probe, a variety of techniques have been developed, which may include amplification of target molecule or amplification of capturing probe, however these methods require extra steps of amplification to increase sensitivity of the detection system.

Different technologies have been developed to separate and/or detect nucleic acids from a liquid sample using a substrate, which includes: separating nucleic acids from a sample by flowing the sample along a bibulous membrane to distribute along the length of the membrane. The separated nucleic acids are further captured by using a capture probes cross-linked on the membrane. In another method, at least two cellular components (such as, genomic DNA, RNA and proteins) are separated, wherein an aqueous solution including the cellular components applied to multiple solid substrates followed by washing. These methods are time consuming and complex as they require multiple steps (such as washing or elution) or multiple substrates. In many of these methods, washing of the substrate is a significant step; however, the washing may dilute or remove the capture probes from the substrate if the probes are not cross-linked to the substrate.

A simplified method for separating nucleic acid from a complex sample for subsequent analysis is highly desirable. Simultaneous capture, separation, amplification, concentration, and detection of nucleic acids are especially required when the quantity of the biological sample is less, for example, the sample procured for biopsy or a sample collected for forensic application. The increased use of nucleic acids requires fast, simple and reliable methods for separating and detecting nucleic acids.

BRIEF DESCRIPTION

In one embodiment, a method of capturing a target nucleic acid is provided, wherein the method comprises applying a nucleic acid capture probe to a capture zone of a substrate, wherein the nucleic acid capture probe having a first molecular weight comprises at least a sequence that is complimentary to at least a portion of the target nucleic acid sequence and the nucleic acid capture probe is substantially immobilized at the capture zone of the substrate; applying a sample comprising the target nucleic acid having a second molecular weight to a sample application zone of the substrate; wherein the sample comprising the target nucleic acid flows across a length of the substrate from the sample application zone to the capture zone by lateral flow, and the target nucleic acid is captured by the nucleic acid capture probes by hybridization at the capture zone, wherein the nucleic acid capture probe is a rolling circle amplification (RCA) product.

In another embodiment, a method of capturing target nucleic acids is provided, wherein the method comprises applying nucleic acid capture probes to a capture zone of a substrate, wherein the nucleic acid capture probes having a first molecular weight comprise at least a sequence that is complementary to at least a portion of the target nucleic acid sequence and the nucleic acid capture probes are substantially immobilized at the capture zone of the substrate; applying a sample comprising the target nucleic acids having a second molecular weight to a sample application zone of the substrate; and flowing a liquid across a length of the substrate from the sample application zone to the capture zone, wherein the target nucleic acids migrate away from the sample application zone to the capture zone by lateral flow and are captured by the nucleic acid capture probes by hybridization.

In yet another embodiment, a method of capturing target nucleic acids is provided, wherein the method comprises applying a nucleic acid capture probe to a capture zone of a substrate, wherein the nucleic acid capture probe having a first molecular weight comprises at least a sequence that is complementary to at least a portion of the target nucleic acid sequence and the nucleic acid capture probe is substantially immobilized at the capture zone of the substrate; applying a sample comprising one or more of the target nucleic acid having a second molecular weight, a template nucleic acid having a third molecular weight to a sample application zone of a substrate; flowing a nucleic acid amplification reaction mixture across a length of the substrate through the sample application zone to the capture zone, wherein the template nucleic acids are amplified to form the target nucleic acids; separating the target nucleic acids from the template nucleic acids by lateral flow, wherein the target nucleic acids migrate away from the sample application zone to the capture zone and are captured by the nucleic acid capture probes by hybridization without a washing step.

BRIEF DESCRIPTION OF THE DRAWINGS

FIG. 3 discloses SEQ ID NOS 8, 7 and 9, respectively, in order of appearance.

FIG. 6A illustrates a lateral flow assay on PEG modified nitrocellulose membranes under conditions of different concentrations of capture probe at room temperature after 1 day and 2 day of drying the membrane, in accordance with an example of an embodiment of the invention.

FIG. 6B illustrates a lateral flow assay on nitrocellulose membranes under conditions of different concentrations of capture probe at room temperature after 1 day and 2 day of drying the membrane, in accordance with an example of an embodiment of the invention.

DETAILED DESCRIPTION

Figure 1:
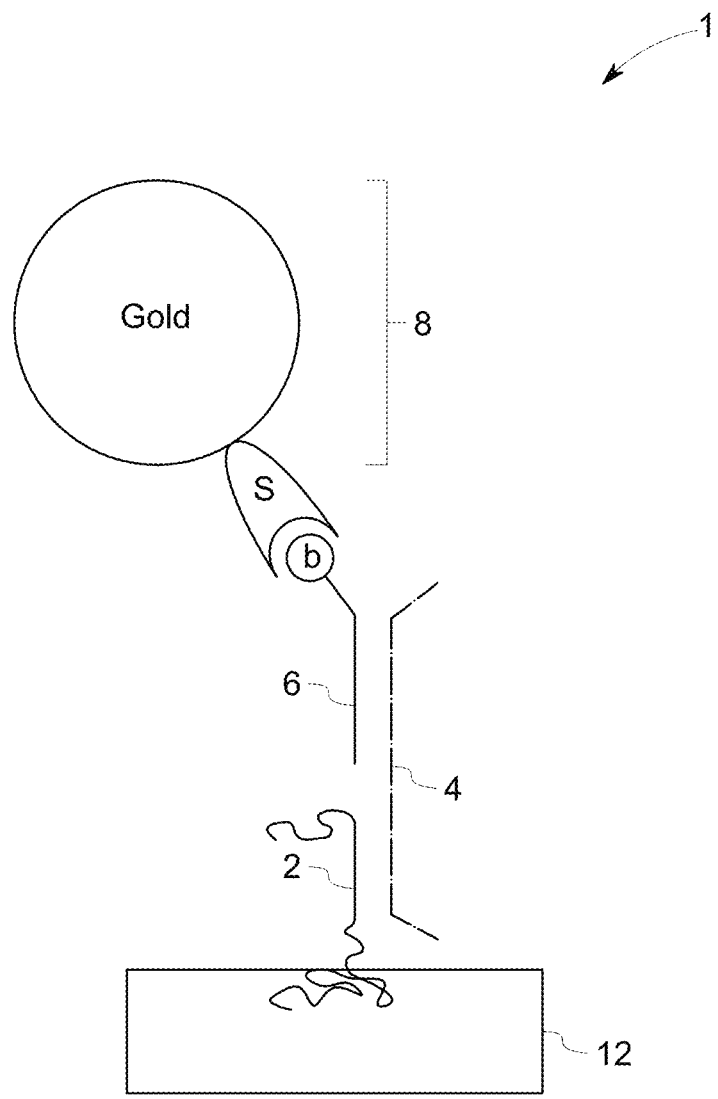
FIG. 1 illustrates a schematic diagram of capture and detection of a target nucleic acid captured using a nucleic acid capture probe in accordance with an example of an embodiment of the invention.

Various embodiments provide suitable methods for separation of target nucleic acids from a biological sample, followed by detection and concentration of the target nucleic acid, such as nucleic acid amplicons from a sample comprising non-target nucleic acids, unwanted contaminants. The target nucleic acids are separated from the biological sample by capturing the target nucleic acids using nucleic acid capture probes based on nucleic acid capture probe-target nucleic acid interaction, such as hybridization. The substrate is configured to collect a biological sample, extract nucleic acids from the sample followed by separation and detection on the same substrate.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The term "nucleic acid" as referred to herein comprises all forms of DNA (e.g. genomic DNA, mtDNA) or RNA (mRNA, tRNA, rRNA, small RNA, siRNA, miRNA, non-coding RNA, animal RNA, plant RNA, viral RNA or bacterial RNA), as well as recombinant RNA and DNA molecules or analogues of DNA or RNA generated using nucleotide analogues. The nucleic acids may be single stranded or double stranded. The nucleic acids may include the coding or non-coding strands. The term also comprises fragments of nucleic acids, such as naturally occurring RNA or DNA which may be recovered using the extraction methods disclosed. Nucleic acid may also refer to a portion of a nucleic acid (e.g., RNA or DNA). The extracted nucleic acids may further comprise peptide nucleic acids (PNA).

Separated nucleic acids may comprise single type of nucleic acids or two or more different types of nucleic acids. The nucleic acids may be single-stranded, double-stranded, linear or circular. Molecular weights of separated nucleic acids are also not limited, may be optional in a range from several base pairs (bp) to several mega base pair (Mbp).

As used herein, the term "target nucleic acid" refers to a nucleic acid (such as DNA or RNA) sequence of either natural or synthetic origin that is desired to be captured by the nucleic acid capture probe. The target nucleic acid is also desired to be detected or additionally to be amplified in an amplification reaction. The target nucleic acid may be obtained from a biological sample in vivo or in vitro. For example, the target nucleic acid may be obtained from a bodily fluid (e.g., blood, blood plasma, serum, or urine), an organ, a tissue, a cell, a sectional portion of an organ or tissue, a cell isolated from a biological subject (e.g., a region containing diseased cells, or circulating tumor cells), a forensic sample or an ancient sample. The biological sample that contains, or is suspected to contain, the target nucleic acid may be of eukaryotic origin, prokaryotic origin, viral origin or bacteriophage origin. For example, the target nucleic acid may be obtained from an insect, a protozoa, a bird, a fish, a reptile, a mammal (e.g., rat, mouse, cow, dog, guinea pig, or rabbit), or a primate (e.g., chimpanzee or human). The target nucleic acid may also be a complementary DNA (cDNA) that is generated from an RNA template (e.g., mRNA, ribosomal RNA) using a reverse transcriptase enzyme. A DNA product generated by another reaction, such as a ligation reaction, a PCR reaction, or a synthetic DNA may also serve as a suitable target nucleic acid. The target nucleic acid may be dispersed in solution or may be added to nucleic acid capture probe immobilized on a solid support, such as in blots, arrays, glass slides, microtiter plates, beads or ELISA plates.

A "template nucleic acid" is defined as a DNA or RNA which may be amplified on a substrate. The DNA may be amplified by a DNA polymerase in a DNA amplification reaction to produce target amplification products or target amplicons.

As used herein, the term "capture probe" or "nucleic acid capture probe" refers to a nucleic acid that comprises at least one sequence that is complementary to at least one sequence of the target nucleic acid. In some embodiments, the nucleic acid capture probe is deoxyribonucleic acid (DNA). In one embodiment, the nucleic acid capture probe is a rolling circle amplification product DNA. The nucleic acid capture probe may comprise multiple sequences that are complimentary to the DNA sequence of the target nucleic acid, such as a target DNA. The capture probe, which is generated by RCA reaction, may comprise nucleotide analogs. In one embodiment, the RCA reaction starts from a circular template and only the original circles are copied by amplification, wherein the nucleotide analogs incorporated into the capture probe may be utilized for generating a probe which has high specificity and improved binding of the template. The nucleic acid capture probe is applied to capture zone of a substrate, wherein the capture probe captures the target nucleic acid by hybridization.

As used herein, the term "sample application zone" refers to an area on a substrate, wherein a sample is applied to that area or zone of the substrate for further processing. The sample application zone is a part of the same substrate. In some embodiments the sample application zone may comprise impregnated reagents, such as stabilizing reagents or cell lysis reagents. The sample application zone may be a paper comprising reagents disposed on the substrate.

As used herein, the term "capture zone" refers to an area on a substrate, wherein the nucleic acid capture probe is immobilized on the substrate. The target nucleic acids of a sample is captured at the capture zone of the substrate and thereby separated from the other non-target materials and/or contaminants of the sample. The capture zone is a part of the same substrate. In some embodiments, the capture zone is also noted as "detection zone" as after capturing the target nucleic acids, detection probes are added to the substrate and the captured nucleic acids are detected by binding with the detection probe at the "capture zone". In some embodiments, the capture zone comprises impregnated detection probes.

"Amplicons" or "amplification product" may include multiple copies of a template nucleic acid or multiple copies of sequences that are complementary to the template nucleic acid. The amplicons may comprise one or more nucleic acid sequence that is complementary to at least a sequence present in the nucleic acid capture probe. The amplicons or amplification products are the "target nucleic acids". The template nucleic acid, such as a template DNA is amplified to produce amplicons, which are referred as target nucleic acids or target nucleic acid amplicons. Either a portion of a target DNA or the entire region of a target DNA may be captured by a nucleic acid capture probe to produce a target nucleic acid amplicons: nucleic acid capture probe complex, wherein the target nucleic acid amplicons and the nucleic acid capture probe are hybridized to each other.

As used herein, the term "substantially immobilized" refers to a quantity of nucleic acid capture probe having certain molecular weights, which are positioned around a particular positioning portion, such as a capture zone on a substrate. The immobilization of the nucleic acid capture probe may occur due to higher molecular weight of the nucleic acids. The nucleic acids having higher molecular weight typically have lower mobility while flowing a buffer along the length of the substrate. The substantial quantity of nucleic acids may be represented as the percentage of the total amount of nucleic acids having a particular molecular weights in the sample solution immobilize at a particular position. For example, substantially the nucleic acid capture probe having first molecular weight means 90% of the total nucleic acid capture probe applied to the substrate immobilized on the substrate at or around the capture zone.

As used herein the term "oligonucleotide" refers to an oligomer of nucleotides. A nucleotide may be represented by its letter designation using alphabetical letters corresponding to its nucleoside. For example, A denotes adenine, C denotes cytosine, G denotes guanine, U denotes uridine, and T denotes Thymine (5-methyl uridine), W denotes either A or T/U, and S denotes either G or C. N represents a random nucleoside and may be any of A, C, G, or T/U. A star (*) sign preceding a letter designation denotes that the nucleotide designated by the letter is a phosphorothioate-modified nucleotide. For example, *N represents a phosphorothioate-modified random nucleotide. A plus (+) sign preceding a letter designation denotes that the nucleotide designated by the letter is a locked nucleic acid (LNA) nucleotide. For example, +A represents an adenosine LNA nucleotide, and +N represents a locked random nucleotide. The oligonucleotide may be a DNA oligonucleotide, an RNA oligonucleotide or a DNA-RNA chimeric sequence. Whenever an oligonucleotide is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide ("Terminal nucleotide" refers to a nucleotide that is located at a terminal position of an oligonucleotide sequence. The terminal nucleotide that is located at a 3' terminal position is referred as a 3' terminal nucleotide, and the terminal nucleotide that is located at a 5' terminal position is referred as a 5' terminal nucleotide).

As used herein the dNTP mixture refers to a mixture deoxyribonucleoside triphosphates, where N is a random nucleotide including any of A, C, G, or T/U.

As used herein, "primer", or "primer sequence" refers to a short linear oligonucleotide that hybridizes to a target nucleic acid sequence (e.g., a deoxyribonucleic acid (DNA)) to prime a nucleic acid amplification reaction. The primer may be a ribonucleic acid (RNA) oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acids under such hybridization conditions. The upper limit is often determined by the possibility of having a duplex formation in a region other than the pre-determined nucleic acids sequences in the target nucleic acids. As a non-limiting example, suitable primer lengths are often in the range of about 4 to about 40 nucleotides long. A primer may also be used to capture a nucleic acid sequence.

As used herein, the terms "amplification", "nucleic acid amplification", or "amplifying" refer to the production of multiple copies of a nucleic acid template, or the production of multiple nucleic acid sequence copies that are complementary to the nucleic acid template.

As used herein, the term "nucleotide analogue" refers to compounds that are structurally similar (analogues) to naturally occurring nucleotides. The nucleotide analogue may have an altered phosphate backbone, sugar moiety, nucleobase, or combinations thereof. Generally, nucleotide analogues with altered nucleobases confer, among other things, different base pairing and base stacking proprieties. Nucleotide analogues having altered phosphate-sugar backbone (e.g., Peptide Nucleic Acid (PNA), Locked Nucleic Acid (LNA)) often modify, among other things, the chain properties such as secondary structure formation.

As used herein, the term "complementary", when used to describe a first nucleic acid/oligonucleotide sequence in relation to a second nucleic acid/oligonucleotide sequence, refers to the ability of a polynucleotide or oligonucleotide comprising the first nucleic acid/oligonucleotide sequence to hybridize (e.g., to form a duplex structure) under certain hybridization conditions with an oligonucleotide or polynucleotide comprising the second nucleic acid/oligonucleotide sequence. Hybridization occurs by base pairing of nucleotides (complementary nucleotides). Base pairing of the nucleotides may occur via Watson-Crick base pairing, non-Watson-Crick base pairing, or base pairing formed by non-natural/modified nucleotides.

As used herein, the term "high stringent hybridization conditions" refer to conditions that impart a higher stringency to an oligonucleotide hybridization event than the stringency provided by conditions that may be used for nucleic acid amplification reactions. Higher stringency hybridization conditions may be desired to prevent oligonucleotide hybridization events that may contain mismatched bases within the resulting hybridized duplex. For example, a high stringent hybridization condition may be achieved in a nucleic acid amplification reaction by increasing the reaction temperature or by decreasing the salt concentration or by including denaturing agents in the buffer such as glycerol or ethylene glycol. Nucleic acid amplification reactions are sometimes carried out at about 75 mM salt concentrations. In contrast, if a nucleic acid amplification reaction is performed at 15 mM salt concentrations, it may offer a high stringent hybridization condition. Highly stringent hybridization conditions may be used in an in-vitro isothermal nucleic acid amplification reaction by increasing the reaction temperature above the typical reaction temperature of 30° C. For example, the isothermal nucleic acid amplification reaction may be performed at about 35° C. to about 45° C.

As used herein, the term "rolling circle amplification (RCA)" refers to a nucleic acid amplification reaction that amplifies a circular nucleic acid template (e.g., single stranded DNA circles) via a rolling circle mechanism. Rolling circle amplification reaction may be initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). Rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the LRCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. Rolling circle amplification may be performed in vitro under isothermal conditions using a suitable nucleic acid polymerase such as Phi29 DNA polymerase.

As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'→3' direction. Since DNA polymerase can only add a nucleotide onto a pre-existing 3'-OH group, to begin a DNA synthesis reaction, the DNA polymerase needs a primer to which it can add the first nucleotide. Suitable primers comprise oligonucleotides of RNA or DNA or nucleotide analogs. The DNA polymerases may be a naturally occurring DNA polymerases or a variant of natural enzyme having the above-mentioned activity. For example, it may include a DNA polymerase having a strand displacement activity, a DNA polymerase lacking 5'→3' exonuclease activity, a DNA polymerase having a reverse transcriptase activity, or a DNA polymerase having an exonuclease activity.

As used herein, the terms "strand displacing nucleic acid polymerase" or "a polymerase having strand displacement activity" refer to a nucleic acid polymerase that has a strand displacement activity apart from its nucleic acid synthesis activity. A strand displacing nucleic acid polymerase can continue nucleic acid synthesis on the basis of the sequence of a nucleic acid template strand by reading the template strand while displacing a complementary strand that is annealed to the template strand. The strand displacing nucleic acid polymerase includes DNA polymerase, RNA polymerase, and reverse transcriptase.

The term, "reducing agents" as referred to herein include any chemical species that provides electrons to another chemical species. A variety of reducing agents are known in the art. Examples of reducing agents include dithiothreitol (DTT), 2-mercaptoethanol (2-ME), and tris (2-carboxyethyl) phosphine (TCEP). Moreover, any combination of these or other reducing agents may be used. In particular embodiments, the reducing agent is TCEP.

The term "amplification buffer" as used herein includes, but is not limited to, 2-Amino-2-hydroxymethyl-propane-1, 3-diol (Tris), 2-(N-morpholino) ethanesulfonic acid (MES), 3-(N-morpholino)propanesulfonic acid (MOPS), citrate buffers, 4-(2-hydroxyethyl)-1-piperazineethanesulfonic acid (HEPES), and phosphate buffers. The amplification buffer further includes, for example, Tris-HCl, diammonium sulphate, monovalent cation (such as KCl), divalent cation (such as $MgSO_4$) or Tween®20. This list of potential buffers is for illustrative purposes only. The pH of the buffer is typically titrated in the range of 6 to 8. In some embodiments, the buffer comprises dNTPs, BSA or combination thereof.

The term "separate, separating or separation" used herein indicates the act or action to isolate or purify target nucleic acids from non-target nucleic acid and/or unwanted contaminants of a sample solution.

The term "sample" or "biological sample" is used in a broad sense and is intended to include a variety of physiological or clinical biological sources that include nucleic acids. Such sources include, without limitation, whole tissues, including biopsy materials and aspirates; in vitro cultured cells, including primary and secondary cells, transformed cell lines, and tissue and blood cells; body fluids such as urine, sputum, semen, secretions, eye washes and aspirates, lung washes and aspirates; media from DNA or RNA synthesis; mixtures of chemically or biochemically synthesized DNA or RNA; fungal and plant tissues, such as leaves, roots, stems, and caps; microorganisms and viruses that may be present on or in a biological sample; bacterial cells; and any other source in which DNA and/or RNA is or may be in.

The sample solution is a solution comprising either or both of DNA and RNA, or, cells, cell components or cell extracts which comprise either or both of DNA and RNA, dissolved, suspended, mixed or otherwise included therein. The sample solution may be a solution prepared from a biological sample.

One or more embodiments of a method of capturing a target nucleic acid are provided, wherein the method comprises applying a nucleic acid capture probe to a capture zone of a substrate, wherein the nucleic acid capture probe having a first molecular weight comprises at least a sequence that is complimentary to at least a portion of the target nucleic acid sequence and the nucleic acid capture probe is substantially immobilized at the capture zone of the substrate. In these embodiments, the method further comprises applying a sample comprising the target nucleic acid having a second molecular weight to a sample application zone of the substrate; wherein the sample comprising the target nucleic acid flows across a length of the substrate from the sample application zone to the capture zone by lateral flow, and the target nucleic acid is captured by the nucleic acid capture probe by hybridization at the capture zone.

The method steps may be described in detail with reference to an illustrative example as shown in FIG. 1. FIG. 1 illustrates, in accordance with one embodiment, a schematic representation 1 of a captured target nucleic acid 4 by a nucleic acid capture probe 2 immobilized on a substrate 12. As noted, the method comprises applying a nucleic acid capture probe 2 to a capture zone of a substrate 12, wherein the nucleic acid capture probe 2 has a first molecular weight. The first molecular weight of the nucleic acid capture probe is high enough to minimize the mobility of the nucleic acid capture probe on the substrate during lateral flow, and the nucleic acid capture probe entangled on the substrate 12, as shown in FIG. 1. The entangled nucleic acid capture probe 2 is substantially immobilized on the substrate 12 and thereby used as a capture probe for capturing a target nucleic acid 4, which may comprise a detection moiety 6. The target nucleic acid 4 is captured followed by detection using, for example, a detection probe 8.

The nucleic acid capture probe 2 captures the target nucleic acid 4 present in an applied sample. The term "capture" may include, but is not limited to, hybridization of the target nucleic acids with the nucleic acid capture probes, physical interaction of the target nucleic acids with the nucleic acid capture probes, or chemical interaction of the target nucleic acids with the nucleic acid capture probes. In one or more embodiments, the target nucleic acid 4 may be labelled with a detector moiety 6, which may be detected by a detector probe 8.

Figure 2:
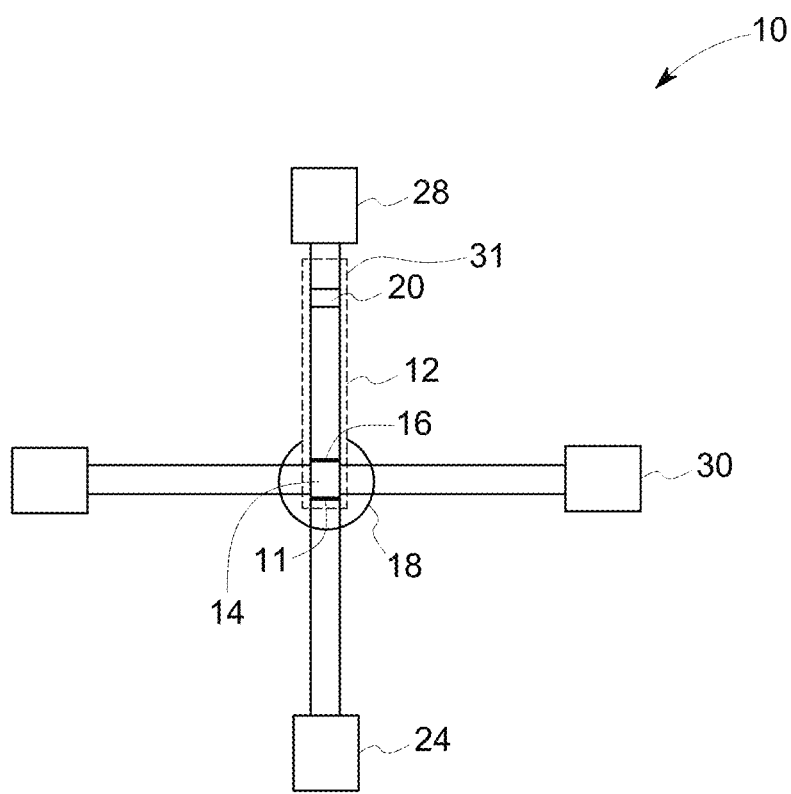
FIG. 2 illustrates a schematic diagram of a device comprising a substrate for lateral flow in accordance with another example of an embodiment of the invention.

To describe the method steps sufficiently, a design of the substrate is briefly described herein to generally correlate the method steps to the substrate components. Referring to FIG. 2, a device 10, in accordance with one embodiment, comprises a substrate 12, with a first end 11 and a second end 31. In some embodiments, the substrate is an elongated strip 12, and the first end 11 and the second end 31 are located at the opposite side of a major axis (such as length) of the substrate 12. The substrate comprises a capture zone 20 adjacent to the second end 31.

The nucleic acid capture probe employed in the method may comprise a high molecular weight nucleic acid, which has low mobility, and may not be able to migrate from one end 11 of a substrate 12 to the other end 31 using a lateral flow. The target nucleic acid 4, which may become captured by the nucleic acid capture probe 2, is generally smaller in size. More particularly, the target nucleic acid 4 having a second molecular weight, which is less than the first molecular weight of the nucleic acid capture probe 2, wherein the target nucleic acid migrates from one end of the substrate 12 to the other end under lateral flow. In some embodiments, the first molecular weight of the nucleic acid capture probe is in a range from about 20,000 bases to about 150,000 bases. In one embodiment, the first molecular weight of the nucleic acid capture probe is 120,000 bases.

In one or more embodiments, the nucleic acid capture probe may be rolling circle amplification (RCA) product, which is synthesized by RCA reaction. As RCA typically produces concatamers comprising tandem repeat units of the circular nucleic acid template sequence complement, the nucleic acid capture probe may also comprise multiple tandem repeat sequences. In some embodiments, the nucleic acid capture probe comprises 20 to 150 nucleotides tandem repeat sequences. The tandem repeat sequences may be of 50 to 100 nucleotides, in some embodiments.

In one or more embodiments, the nucleic acid capture probe comprises single stranded nucleic acids, such as single stranded DNA (ss DNA) or single stranded RNA (ss RNA). The nucleic acid capture probe may comprise a circular single stranded nucleic acid, a nicked nucleic acid or a linear nucleic acid with specific sequence (s) complementary to one or more sequences of the target nucleic acid. In one embodiment, the nucleic acid capture probe comprises at least a sequence that is complimentary to at least a portion of the target nucleic acid sequence. In some embodiments, the nucleic acid capture probe may comprise multiple copies of a particular sequence or may be referred as a repeat sequence. In these embodiments, the nucleic acid capture probe may comprise multiple sequences that are complimentary to at least one sequence of the target nucleic acid, wherein multiple target nucleic acids may be captured by the single capture probe with multiple repeat sequences.

In one or more embodiments, the nucleic acid capture probe comprises deoxyribonucleic acids (DNA), ribonucleic acids (RNA), nucleic acid analogues or combinations thereof. The nucleic acid capture probe may comprise the nucleotide analogues, which are structurally similar (analogues) to naturally occurring nucleotides. The nucleotide analogue may have an altered phosphate backbone, such as phosphate-sugar backbone often modify, among other things, the chain properties such as secondary structure formation. The nucleic acid capture probe may comprise the nucleotide analogues, such as Peptide Nucleic Acid (PNA) or Locked Nucleic Acid (LNA). In some embodiments, the nucleic acid capture probe may be a cDNA or a genomic DNA of high molecular weight. The nucleic acid capture probe may be a synthetic nucleic acid or a natural nucleic acid. It may also comprise modified nucleotides.

In some embodiments, the nucleic acid capture probe is substantially immobilized at the capture zone of the substrate. A quantity of nucleic acid capture probe having certain molecular weights, such as between 20 kb to about 150 kb, may be positioned around a particular positioning portion, such as a capture zone 20 of a substrate 12. The immobilization of the nucleic acid capture probe on a lateral flow substrate may occur due to higher molecular weight of the nucleic acid of the capture probe. Typically, the nucleic acids having higher molecular weight have lower mobility while the nucleic acids flow across the length of the lateral flow substrate. A percentage of the total amount of nucleic acid capture probe having a particular molecular weight applied to a particular position is referred as a substantial amount of nucleic acid capture probe that immobilized (or substantially immobilized) on the substrate. The substantial nucleic acid capture probe having a first molecular weight may be, for example, 90% or more of the total nucleic acid capture probe applied to the capture zone of the substrate.

The nucleic acid may be attached to a substrate by a mechanical interaction. In one or more embodiments, the nucleic acid, such as DNA is adhered on the substrate surface, by a mechanical interaction, which includes but is not limited to, an entanglement. In some embodiments, the nucleic acid capture probe is immobilized on the substrate by nucleic acid entanglement with the substrate (FIG. 1). The nucleic acid may be entangled on the substrate surface, wherein the interaction between the nucleic acid capture probe and the substrate is stable enough to resist the dissociation of nucleic acid capture probe from the substrate during lateral flow of a liquid through the substrate, for example, in case of washing, the nucleic acid capture probe is retained on the substrate.

The present method employs high molecular weight RCA nucleic acid as capture probe which is immobilized on the substrate by entanglement, unlike the methods where the nucleic acid needs to be cross-linked on the substrate for immobilization. Nucleic acid cross-linking on a substrate (matrix) for nucleic acid detection by lateral flow is known in the art, which is also reported in Asian Biomedicine, Vol. 6, No. 3, 2012; 459-463; "Sensitivity enhancement of nucleic acid detection by lateral flow strip test using UV crosslink method" (Mongokol et al.). The cross-linking is a separate process to immobilize the nucleic acid on the substrate which requires time, resources and effort. The methods of immobilization of nucleic acid on a membrane by cross-linking followed by hybridization are reported in Curr Protoc Immunol., 2001 May; Chapter 10:Unit 10.6A. doi: 10.1002/0471142735.im1006as06; Anal Biochem. 1985 Aug. 15; 149(1):229-37, "Quantitative molecular hybridization on nylon membranes" (Cannon G, Heinhorst S, Weissbach A); and in Biotechniques. 1990 May; 8(5): 478-82. "Parameters affecting hybridization of nucleic acids blotted onto nylon or nitrocellulose membranes" (Twomey TA1, Krawetz SA). However, the present method of immobilizing RCA nucleic acid on the substrate for lateral flow test obviate the requirement of such cross-linking technology for immobilization of nucleic acid on different substrates.

For example, pDNA has been used for capture probe for different lateral flow assay, wherein the pDNA requires UV cross-linking for attaching to the substrate, which is an additional step for preparation of the capture probe bound to a substrate. pDNA is able to cross-linked to the substrate (matrix). The cross-linking may be performed by using UV light, called UV cross-linking. The UV-immobilization of pDNA capture probes on a nitrocellulose strip by cross-linking activity for lateral flow test have been reported in U.S. Patent Application Publication No. US 2012/0015358 A1 (Scarr et al.). The pDNA is pyranosylnucleic acids (pNAs or pDNA), which are isomeric to the natural RNA, in which the pentose units are present in the pyranose form and repetitively linked by phosphodiester groups between the positions C-2' and C-4'. pDNA capture probes have been reported in U.S. Pat. No. 7,153,955 B2 (Miculka et al.). Use of RCA capture probe reduces the step of cross-linking and simplifies the process.

Moreover, the use of a high molecular weight RCA nucleic acid product (such as RCA DNA), which generally comprises tandem repeat sequences, reduces the steps of artificially making the nucleic acid capture probe with multiple repeat sequences and linkers. Further, the use of multiple repeat sequences in the nucleic acid capture probe (RCA DNA), which are complementary to one or more sequences of the target nucleic acid, ensures a strong hybridization and capture of target nucleic acid. The nucleic acid capture probe present on a substrate captures the target nucleic acid with high efficiency when a sample comprising the target nucleic acid is applied to the substrate.

As noted, the sample is applied to a sample application zone of the substrate, which may be present at either end of the substrate. Now referring to FIG. 1, in accordance with one embodiment, the device 10 comprises a substrate 12, with a first end 11 and a second end 31. The substrate 12 comprises a sample application zone 14, wherein the sample may be applied by any means, such as by pipetting. The sample application zone 14 may be adjacent to first end 11 and the capture zone 20 is located at the opposite end of the sample application zone 14, adjacent to the second end 31 of the substrate. As noted, the device 10 further comprises a wicking pad 28 and a stopping pad 30. The sample application zone 14 may also be used as a sample lysis zone and/or nucleic acid stabilization zone. The substrate optionally contains a heating unit 18 at or near the sample application zone for drying the loaded sample.

In some embodiments, the method comprises applying a sample comprising a target nucleic acid to a sample application zone of a substrate; wherein the sample is in a liquid form, such as a sample solution. A sample solution, a liquid, an amplification reagent or a washing solution may be applied to the sample application zone 14. Non-limiting examples of the term "applying" include, contacting or disposing a sample or an amplification reagent or a washing solution on the substrate using a tube, swab, pipette, catheter, syringe, conduit, an automatic injector, or using any other applicable ways/tools. In some embodiments, the sample may be poured onto the substrate.

The sample applied to the substrate, may be a biological sample, which is procured from physiological or clinical biological sources that comprise nucleic acids. In some embodiments, the sample is nucleic acid, in some other embodiments, the sample is a media from DNA or RNA synthesis; mixtures of chemically or biochemically synthesized DNA or RNA, wherein the sample is applied directly to the substrate followed by amplification, separation and capture. In some embodiments, the sample is an amplification product or amplicon.

The nucleic acid may be extracted from cells using cell-lysis when the sample includes cells or tissue. For example, when the sample is collected from blood, thin sliced tissue, tissue culture cells, bacterial cells, body fluids such as urine, sputum, semen, secretions comprising DNA and/or RNA, sample is treated with a lysis reagent after or before applying it to the substrate. As such, in these embodiments, the method typically further comprises contacting the sample with a lysis reagent.

The sample may be pre-treated prior to applying to the sample application zone 14 with an additional lysis reagent for lysing cells which are difficult to lyse. For example, cells of *Mycobacterium tuberculosis*, which have a complex cell-wall structure that is impermeable and difficult to lyse, may be pre-treated with a lysis reagent before applying to the substrate.

In some embodiments of the method, the sample itself comprises a lysis reagent. In some other embodiments, the lysis reagent is impregnated in the sample application zone 14 of the substrate. The cells are lysed when contacted with the lysis reagents to extract nucleic acids from the cells. An example of a method for preparing a sample solution comprising nucleic acids from a biological sample comprises the step of lysing the biological sample using a lysis reagent, wherein the lysis reagent comprises chaotropic substances and/or other reagents.

As noted, the sample comprising the target nucleic acid flows across a length of the substrate from the sample application 14 zone to the capture zone 20 by lateral flow. The movement of the flow across the length of the substrate is referred to herein as a "lateral flow". In lateral flow movement, a liquid migrates under a gravitational force that is parallel to a slope of a substrate on which the liquid is disposed. The lateral flow movement of a liquid enables the target nucleic acids to migrate from one end 11 of a longitudinal substrate 12 to the other end 20.

In some embodiments, the applied sample may be allowed to dry and need to rehydrate for separation from the sample. In these embodiments, the method further comprises flowing a liquid across the length of the substrate from the sample application zone to the capture zone, wherein the target nucleic acids migrate away from the sample application zone to the capture zone by lateral flow. Drying may include activation of a heating element 18, which may be present underneath or adjacent to the sample application zone 14. In these embodiments, the liquid, such as a buffer flows across a length of the substrate from the sample application zone to the capture zone and the dried sample may be rehydrated by applying a liquid. The dried target nucleic acid may be rehydrated by the liquid, such as a buffer, and reconstituted to a solution comprising the target nucleic acid, which migrates away from the sample application zone 14 to the capture zone 20 by lateral flow.

In some embodiments, the liquid comprises a buffer, an amplification reaction mixture, a washing solution, or combinations thereof. In one embodiment, the liquid may flow through the sample application zone along the length of the substrate for washing the substrate. In some embodiments, the liquid is an amplification buffer. In some other embodiments, the liquid is a washing buffer.

Figure 3:
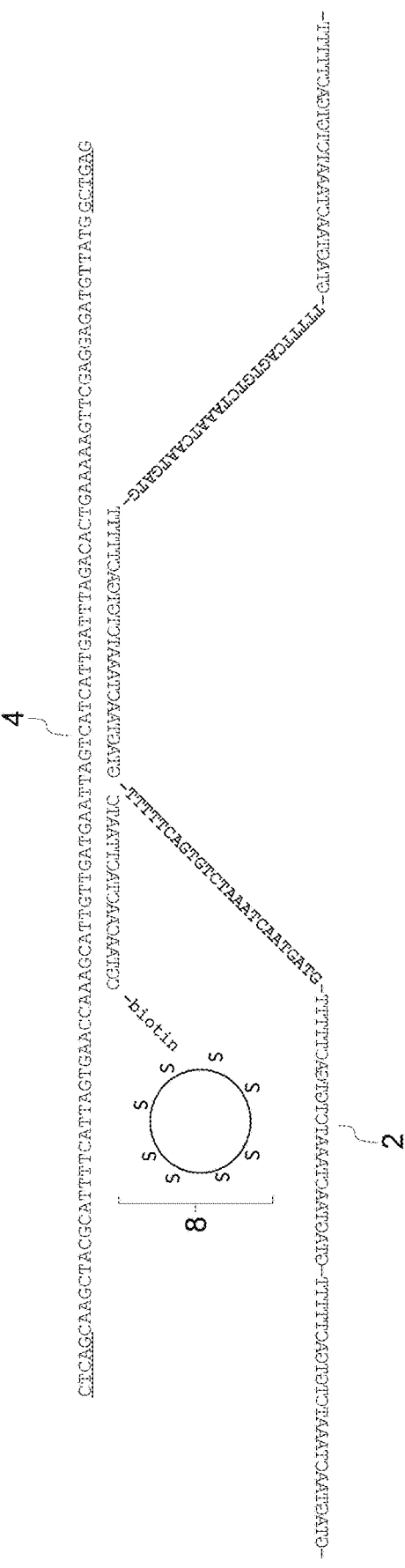
FIG. 3 illustrates a schematic diagram of nucleic acid capture probe, target nucleic acid, detection probe in accordance with another example of an embodiment of the invention.

In some embodiments of the method, the target nucleic acid is captured by nucleic acid capture probe by hybridization. In these embodiments, the nucleic acid/oligonucleotide sequence of the nucleic acid capture probe hybridizes (e.g., to form a duplex structure) under certain hybridization conditions with an oligonucleotide or polynucleotide of a target nucleic acid/oligonucleotide sequence. Hybridization occurs by base pairing of nucleotides (complementary nucleotides), wherein the base pairing of the nucleotides may occur via Watson-Crick base pairing, non-Watson-Crick base pairing, or base pairing formed by non-natural/modified nucleotides. FIG. 3 illustrates, in accordance with one embodiment of the invention, the hybridization pattern of a target nucleic acid sequence 4 with the nucleic acid capture probe sequence 2.

In some embodiments, the oligonucleotide hybridization event occurs under a higher stringency condition than the stringency provided by condition for nucleic acid amplification reactions. Higher stringency hybridization conditions may be desired to prevent oligonucleotide hybridization events that may contain mismatched bases within the resulting hybridized duplex. For example, a high stringent hybridization condition may be achieved in a nucleic acid amplification reaction by increasing the reaction temperature or by decreasing the salt concentration or by including denaturing agents in the buffer such as glycerol or ethylene glycol. In an illustrative embodiment, 15 mM salt concentration may offer a high stringent hybridization condition. Highly stringent hybridization conditions may be used by increasing the reaction temperature above the typical reaction temperature of 30° C.

Figure 4A:
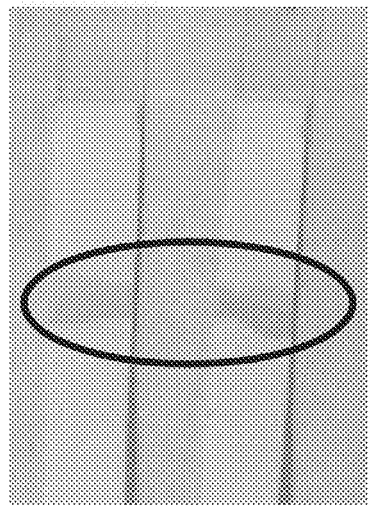
FIG. 4A illustrates a lateral flow assay on membranes under condition of room temperature in accordance with an example of an embodiment of the invention.
Figure 4B:
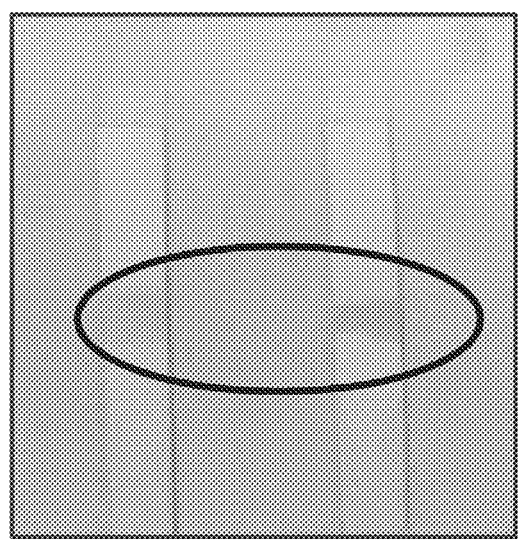
FIG. 4B illustrates a lateral flow assay on membranes under conditions of high temperatures in accordance with an example of an embodiment of the invention.

The RCA product, used as capture probe has the characteristic features which are advantageous for use under high stringency hybridization conditions. As noted, the nucleic acid capture probe is an RCA product, the capture probe may be referred as "RCA capture probe". The target nucleic acid when captured by RCA capture probe followed by detection using biotin-streptavidin detection probe, wherein the detection performance shows by band on the substrate. Due to increased length and high melting temperature of RCA capture probe, the detection performance of the capture probe remains the same either at room temperature or at 50° C., as shown in FIGS. 4A and 4B respectively. This is an improvement over traditional pDNA capture probe where capture may be limited to room temperature or slightly elevated temperature because of the low melting temperature of pDNA probes.

Figures 5A, 5B:
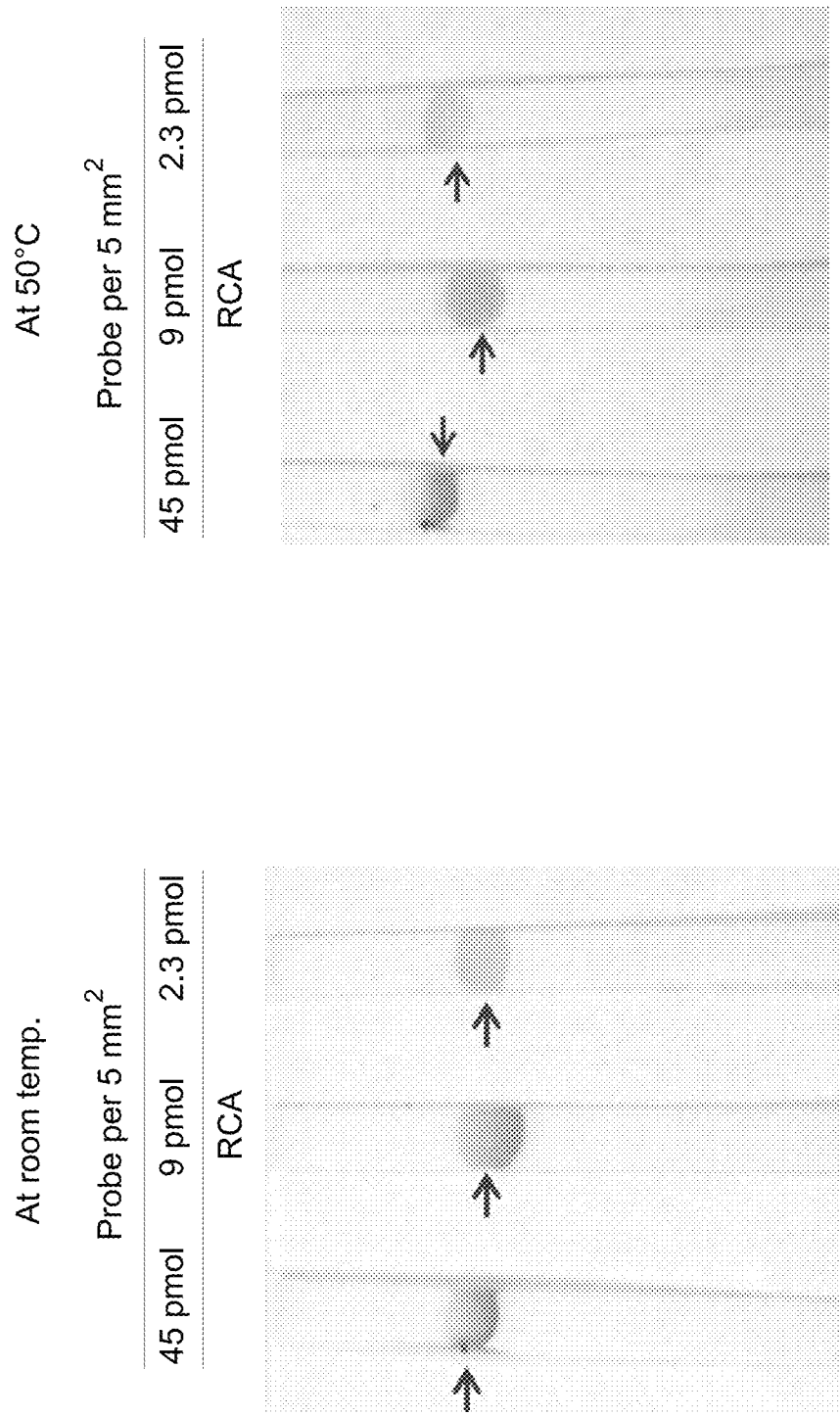
FIG. 5A illustrates a lateral flow assay on membranes under conditions of different concentrations of capture probe at room temperature in accordance with an example of an embodiment of the invention.
FIG. 5B illustrates a lateral flow assay on membranes under conditions of different concentrations of capture probe at high temperature in accordance with an example of an embodiment of the invention.
Figure 5C:
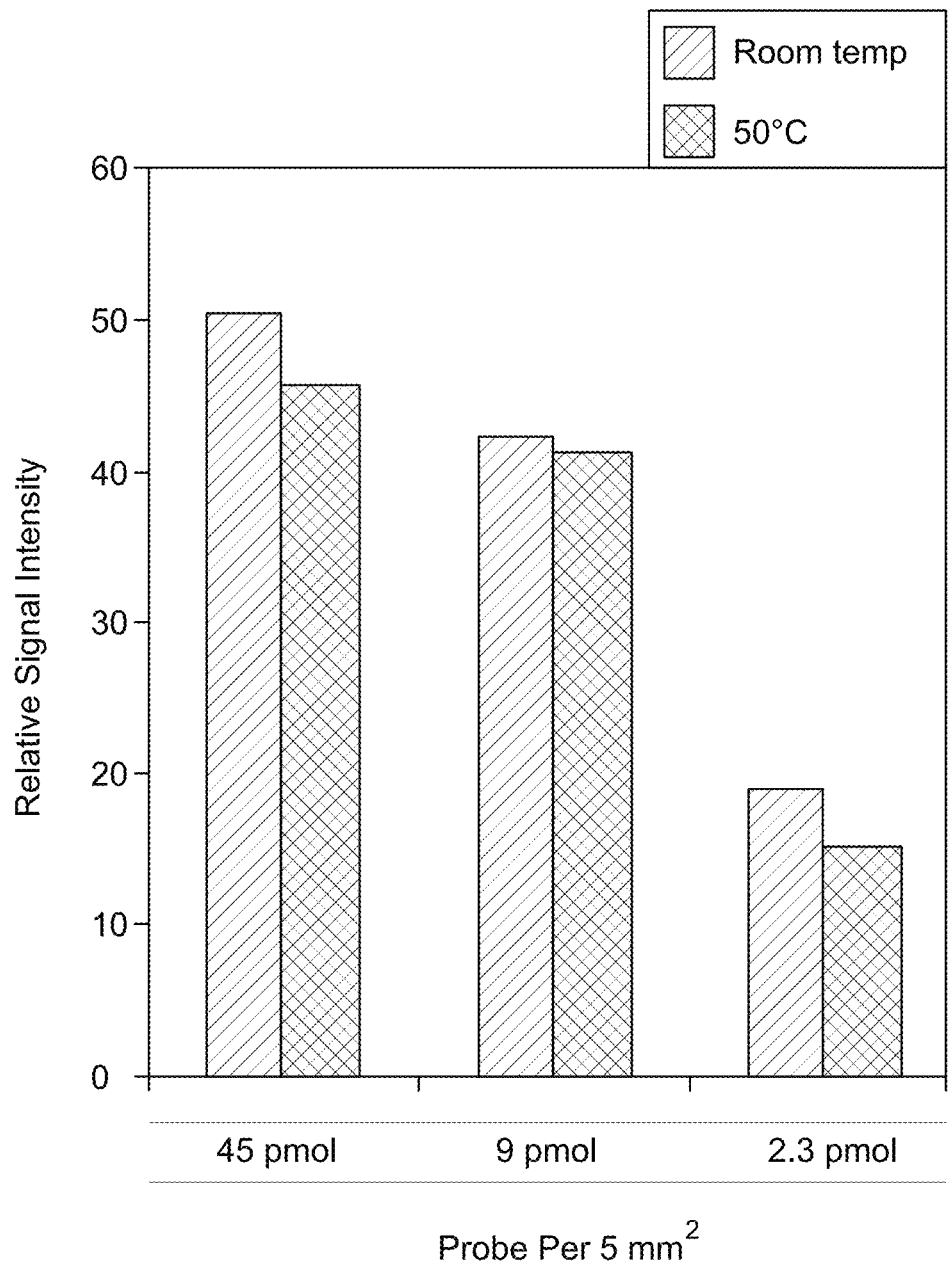
FIG. 5C illustrates a graph showing signal intensity generated from FIGS. 5A and 5B in accordance with an example of an embodiment of the invention.

The lateral flow test sensitivity is independent of temperature condition under different capture probe concentrations, as illustrated in FIGS. 5A and 5B. The signal intensity of bands for a lateral flow detection test increases when the RCA probe concentration on a nitrocellulose membrane is increased, under room temperature as well as at high temperature, as shown in FIGS. 5A, 5B and 5C.

The use of RCA capture probe in lateral flow detection shows similar efficiency on nitrocellulose substrate or modified nitrocellulose substrate, such as pegylated nitrocellulose membrane. The signal intensity of the captured target nucleic acid increases when the RCA capture probe applied to the substrate and dried for two (2) days compared to one (1) day, as shown in FIGS. 6A and 6 B.

In one or more embodiments, the method further comprises flowing a buffer through the sample application zone along the length of the substrate for washing the substrate. In some embodiments, the buffer comprises an amplification buffer. In some embodiments, the amplification reagent and wash solution may be added upstream of the sample application zone.

In some embodiments, a washing liquid, such as an amplification buffer is added to the substrate for washing the substrate, the amplification buffer carries away the impurities from the substrate wherein the sample solution is applied. There are different affinities between the impurities and the substrate; and between the nucleic acids and the substrate, which helps in eliminating the needs for instruments to generate the external driving force (e.g. centrifugation force and pressure) and personnel with specific skills for separation of target nucleic acids from a sample on site and in remote areas. It appears that by flowing a washing liquid, such as an amplification buffer through the sample application zone removes the impurities or non-target nucleic acids away, and the target nucleic acids become sufficiently separated from other components in the sample solution.

As noted, the sample application zone may further comprise lysis reagents or stabilizing reagents, or the lysis reagents may be added to the sample before or after applying to the substrate, wherein the washing step results in removing the lysis reagents, and/or stabilizing reagents impregnated in and/or present on the substrate. The lysis reagents, stabilizing reagents or other impurities and/or non-target nucleic acid may inhibit downstream applications, such as amplification. In some embodiments, the nucleic acid amplification reaction mixture washes one or more inhibitors present on the substrate. The inhibitors or contaminants may also result from cell lysis, such as cell-debris or other cellular organelle, which have inhibitory effect on downstream processes and are removed by washing.

In some embodiments, the method further comprises flowing a washing buffer along the substrate. The term "washing buffer" may interchangeably be used herein as a wash buffer or washing reagent or wash reagent. Referring to FIG. 1, the wash reagent may be stored in a wash reagent reservoir 26, and the wash reagent is flowed from the reservoir 26 to the wash reagent wicking pad 30 through the sample application zone 14. The wicking force inherent from the porosity of the bibulous substrate, such as a quartz fiber filter itself acts as the driving force to enable the amplification buffers to flow along the quartz fiber filter and through the sample application zone. The wicking pads 28, 30 draw the liquid sample, or amplification buffer or the wash buffer to flow towards the wicking pad 28, 30 based on its strong wicking force.

In some embodiments, the wash reagent and the amplification buffer are the same, and may be stored in a single reservoir. The amplification buffer may comprise amplification reagents except an enzyme, such as polymerase. In these embodiments, the washing solution may be replaced by amplification buffer, which may eliminate the step of washing by combining the two steps, such as washing and separation of nucleic acids into one. In these embodiments, the nucleic acids are washed by diffusion of amplification buffer over the substrate 12. The washing buffer or amplification reagent solution flows along the substrate 12 under the wicking force, wherein no external force is used, and carries away the impurities having a less affinity to the substrate (such as quartz fiber filter) than affinity of target nucleic acids. In the embodiments of washing, the nucleic acid capture probe is immobilized on the substrate and is not affected by the lateral flow of the washing liquid. In some embodiments, by applying the washing liquid, the target nucleic acid migrates from sample application zone to the capture zone and captured by the nucleic acid capture probe by hybridization.

In one or more embodiments, the liquid is a nucleic acid amplification reaction mixture that amplifies template nucleic acids present in the sample to form the target nucleic acid amplification product or target amplicon. In these embodiments, the target nucleic acid formed by amplification of a nucleic acid template present in the applied sample. In these embodiments, the method further comprises flowing a nucleic acid amplification reagent across a length of the substrate through the sample application zone. The terms "amplification reagent" and "amplification reagent solution" are interchangeably used hereinafter. The amplification reagent comprises a mixture of dNTP's, oligomer (primer), enzyme(s) including polymerase and amplification buffer.

In some embodiments, the amplification buffer, comprising a mixture of dNTP's, oligomer (primer), buffer and salts, is added to the substrate to rehydrate the substrate. To start the amplification reaction, the enzyme is added to the substrate separately. In some embodiments, the amplification reaction mixture starts amplification in the presence of the amplification buffer when in contact with the template nucleic acids at the sample application zone, wherein the amplification reaction mixture contains the enzyme. In some embodiments, the amplification reagents comprising dNTP mixture, oligomers, and amplification buffer reagents may be impregnated in the substrate, which may be reconstituted using an aqueous buffer. In these embodiments, the DNA polymerase is added before starting the amplification reaction. The amplification reagents may also comprise modified nucleotides.

Referring to FIG. 2, the amplification reagent may be stored in an amplification reagent reservoir 24. The substrate comprises on or more fuses 16 to hold the reagents and releases when it is required. On completion of washing, the fuses 16 are dissolved and the lateral flow of amplification reagent starts flowing from the amplification reagent reservoir 24 and passes through the sample application zone 14 and the capture (detection) zone 20 and reaches the amplification reagent wicking pad 28. The wicking pad generates a wicking force which enables the lateral flow of amplification reagent to migrate towards the wicking pad 28, across the length of the substrate.

In one or more embodiments, the amplification reagent flows through the substrate to amplify the template nucleic acid to form a nucleic acid amplification product (amplicons), which is referred to herein as "target nucleic acid" or "target amplicon". In some embodiments, the nucleic acid capture probe has a first molecular weight, a sample comprising one or more of the target nucleic acids having a second molecular weight, and a template nucleic acid having a third molecular weight. In these embodiments, the sample comprises both of the target nucleic acids having a second molecular weight, and a template nucleic acid having a third molecular weight, which is applied to the sample application zone of the substrate 12. In some other embodiments, the sample comprises template nucleic acid having a third molecular weight, and not the target nucleic acid of second molecular weight. In these embodiments, as noted earlier, the template nucleic acid is amplified to form the amplicons, which are target nucleic acid or target amplicons having second molecular weight and has affinity for the nucleic acid capture probe having first molecular weight. In these embodiments, the template nucleic acid having a third molecular weight is substantially immobilized at the sample application zone 14 and the amplification product having a second molecular weight migrates away from the sample application zone 14 to the capture zone 20 by the lateral flow. As noted, the terms "first", "second", "third" and the like, as used herein do not denote any order, quantity, or importance, but rather are used to distinguish one element from another.

Figure 7:
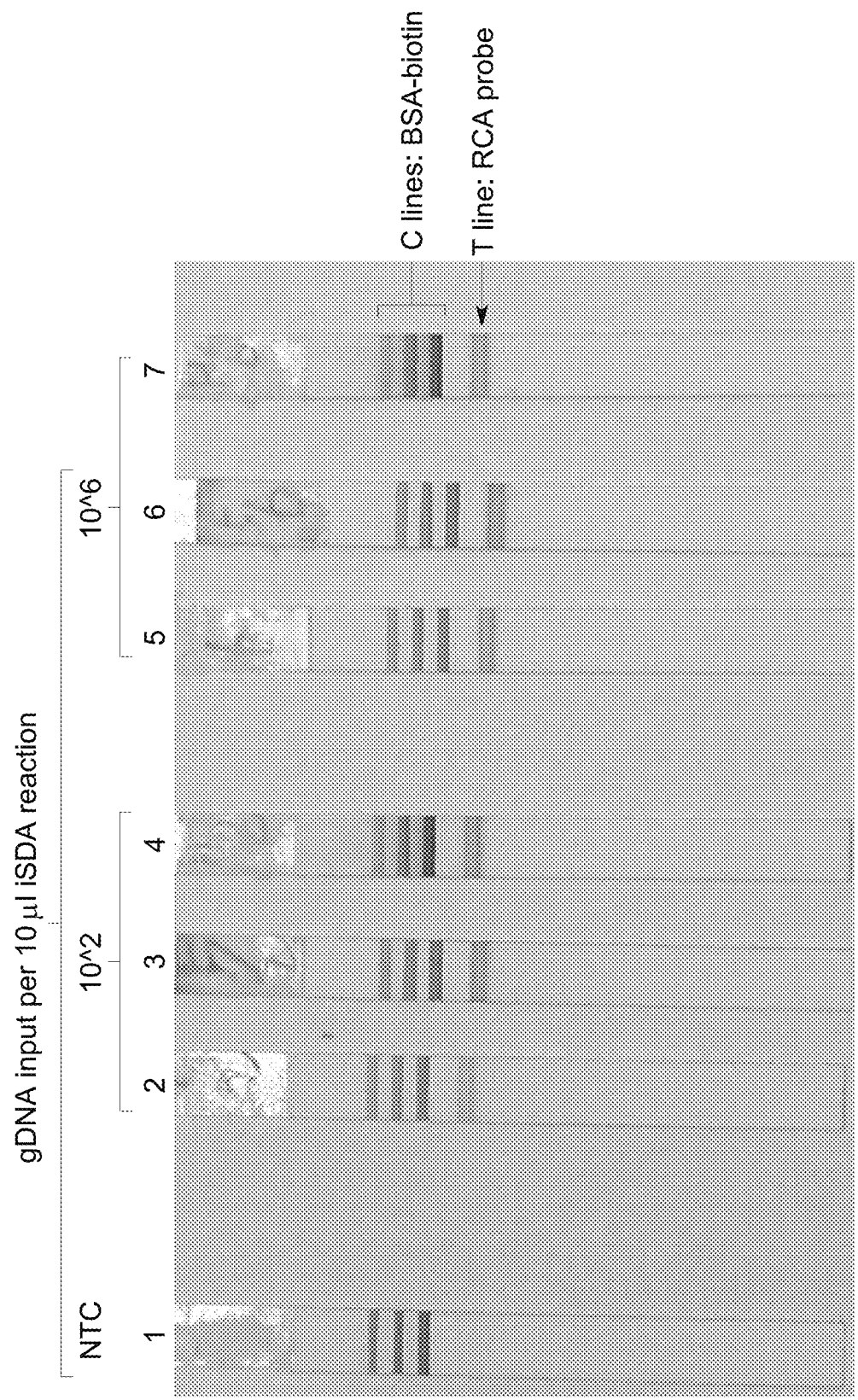
FIG. 7 illustrates a lateral flow assay on nitrocellulose membrane for different input concentration of genomic DNA for isothermal DNA amplification reaction under conditions of different temperature and different drying times of the nucleic acid capture probe, in accordance with an example of an embodiment of the invention.

The nucleic acids having a third molecular weight may be substantially positioned around the sample application zone 14. The target nucleic acids or amplicons having a second molecular weight are substantially captured by the nucleic acid capture probe, such as RCA capture probe, as shown in FIG. 7 and the captured target amplicons are substantially positioned around the capture zone (or detection zone) 20. The term "substantially" used herein refers to a quantity of nucleic acids having certain molecular weights and positioned around the positioning portion, which may be at least about 15% of the total amount of nucleic acids having the molecular weights in the sample solution retains at the particular position, at least 50% of the total amount of nucleic acids having the molecular weights in the sample solution retains at the particular position, or at least 90% of the total amount of nucleic acids having the molecular weights in the sample solution retains at the particular position. For example, substantially the nucleic acids with third molecular weight means 90% of the total template nucleic acids applied to the substrate retains at the substrate at or around the sample application zone 14, and for target nucleic acids with second molecular weight, 90% of the total amplified nucleic acids generated on the substrate retains at the substrate at or around the length of the substrate or, specifically, at or around the capture zone (or detection zone) 20.

In some embodiments of methods, the amplification begins as the amplification reagents enter the sample application zone 14. In some embodiments, the amplification reaction starts when impregnated amplification reagents are rehydrated to reconstitute the reagents and nucleic acid polymerase added to the substrate. The amplification reagent may continue to flow through the capture zone 20 to the wicking pad 28. The amplification reagent may move from the reservoir to the wicking pad via a lateral flow, without forming a bolus. The amplification products may be captured in the capture zone 20 by one or more nucleic acid capture probe, such as RCA capture probe. In some embodiments, the methods provide a continuous flow of amplification reagents and the amplification products through the capture zone (or detection zone) 20. In these embodiments, the continuous flow of target amplicons or target nucleic acid to the capture zone results in repeated capture of the target nucleic acid or amplicon by the nucleic acid capture probe. This method accumulates large amount of target nucleic acid at the capture zone, which is easily detectable as the concentration of the target nucleic acid is quite high at the capture zone. Further, this may be a way of accumulating target nucleic acid after separation from a sample, wherein the sample may be a complex sample comprising multiple similar components. The method results in concentrating a particular target nucleic acid from a dilute sample by repeated flow through the substrate, which further decrease heterogeneity of the target in a solution when eluted from the capture probe.

In some embodiments, the method comprises flowing the nucleic acid amplification reaction mixture which separates the template nucleic acids and the target nucleic acid amplification product according to their molecular weights. The template nucleic acids have third molecular weight and the amplified target nucleic acids have second molecular weight, wherein the difference between the molecular weight may enable the amplified target nucleic acids to be separated from the template nucleic acids during lateral flow. As can be seen from the examples, after diffusion of the amplification reagents through the sample application zone 14 along the length of the substrate 12, nucleic acids are positioned on the quartz fiber filter 12 according to the molecular weights thereof. To be specific, nucleic acids having higher molecular weights are positioned closer to the sample application zone 14 than nucleic acids having lower molecular weights, which are captured at the capture zone by nucleic acid capture probe of first molecular weight.

The sample application zone 14 is a positioning portion for the template nucleic acids having the third molecular weight. A substantial portion of the nucleic acids having a third molecular weight are positioned around the sample application zone 14. In some embodiments, the third molecular weight is in a range of at least about 50 kb. In some embodiments, the third molecular weight is in a range from about 50 kb to about 150 kb. In some embodiments, about 50 kb refers to a range of 50 kb±15 kb.

In some embodiments, substantial portion of the nucleic acids having a second molecular weight are positioned around the second end 31. In this case, the second end 31 is the positioning portion for the target nucleic acids having the second molecular weight, as well as the nucleic acid capture probe having a first molecular weight. The target nucleic acids having second molecular weight may be distributed across the substrate. In some embodiments, the second molecular weight is in a range of less than about 50 kb. In some embodiments, the target nucleic acid amplicons may have more than one molecular weight population, which may results from more than one template molecules.

In some embodiments of the method, one or more amplification reactions occur on the substrate. In some embodiments, a first amplification reaction occurs at the sample application zone to generate a first amplification product (or first target nucleic acid). One or more amplification reactions may occur during migration of the first amplification product or first target nucleic acid. Similarly, one or more amplification reactions may occur during migration of the second amplification product or second target nucleic acid, and so on. Multiple amplification reactions generate plurality of target amplification products, which facilitates detection method with greater ease, sensitivity and accuracy. In these embodiments, the nucleic acid capture probe also comprise one sequence or multiple sequences which are complimentary to one or more sequences of the first target nucleic acid amplicon or the second target nucleic acid amplicon, and capture the first target nucleic acid amplicon or the second target nucleic acid amplicon by hybridization. Especially, the multiple amplification reactions are useful when the template nucleic acid is available in a trace quantity, for example, sample procured for forensic application or from biopsy sample.

In some embodiments, the amplification occurs on the substrate to generate target nucleic acid is an isothermal amplification reaction. The isothermal amplification may include, but is not limited to; rolling circle amplification (RCA), multiple displacement amplification (MDA), helicase dependent amplification (HDA), ping pong amplification, cross priming amplification (CPA), recombinase polymerase amplification (RPA), loop mediated isothermal amplification (LAMP) and strand displacement amplification (SDA).

In different embodiments, the primary detection probe (or detection probe) may be coupled to different molecules, substrate, or may be added separately. For examples, the substrate comprises detection probes, nucleic acid capture probe comprises the detection probe, amplified target nucleic acid comprises detection probe or the detection probe may separately be added during, prior or on completion of the amplification reaction or capture of the target nucleic acid.

In some embodiments, the target nucleic acid present in a sample is labelled with a detectable moiety, which may include but is not limited to, an affinity tag, a dye, an enzyme substrate, or a magnetic probe. In an illustrative embodiment, the affinity probe is biotin, which is relatively small (244.3 Daltons) ligand and may be conjugated to many proteins and other molecules with minimum alteration of its biological activity. The biotin tag may be used to facilitate detection with a biotin-binding protein that is conjugated to an enzyme, fluorophore or other reporter molecule. An optimized biotin-to-probe ratio may greatly increase the signal output of a detection system, which provide adequate signal for detection system.

The method further comprises detecting the target nucleic acids by using a primary detection probe. The target nucleic acid may comprise the primary detection probe. In some embodiments, the nucleic acid capture probe comprises a primary detection probe. The primary detection probe may comprise a chromophore moiety, a fluorescent moiety, a phosphorescence moiety, an affinity probe, a magnetic probe, a paramagnetic probe or combinations thereof. The primary detection probe may further comprise a binding moiety such as a biotin or an antibody, a streptavidin, a gold particle or combinations thereof.

In some embodiments, the method further comprises flowing a solution comprising a secondary detection probe along the length of the substrate. In these embodiments, the secondary detection probe binds to the primary detection probe, wherein the primary detection probe previously bound to the captured target nucleic acids. In some other embodiments, the secondary detection probe binds to the primary detection probe, wherein the primary detection probe previously bound to the nucleic acid capture probe.

The amplified target nucleic acids or amplicons may be captured at the capture zone, followed by detection of the target nucleic acid on the substrate. In some embodiments, a solution comprising one or more detection probes is added to the substrate. In some other embodiments, the detection probes are part of the amplification reaction mixture. A solution comprising one or more detection probes or an amplification reaction mixture comprising one or more detection probes may be flowed along the length of the substrate. In some embodiments, the detection probes may directly be added to the capture zone or detection zone 20. In some examples, the detection probes in a form of solution or as a part of an amplification reaction mixture is applied at the capture zone or detection zone 20.

The nucleic acid capture probes may capture the amplified target nucleic acids of interest on the substrate during diffusion of the nucleic acid on the substrate. The amplification product (target nucleic acid) may be immobilized on the substrate by a physical interaction with the nucleic acid capture probe, wherein the nucleic acid capture probe is labelled with a detection probe.

The "detection probe" may detect the target nucleic acid or target nucleic acid amplicons using one or more detection method. The detection probes may include, but are not limited to, gold particles, antisense oligomer, pyrophosphate, phosphatase, biotin-streptavidin beads, antibody, fluorescence resonance energy transfer (FRET) probes, horseradish peroxidase (HRP) probes and luciferase. The antisense oligomers may comprise of natural nucleotides or nucleotide analogs. The oligonucleotides may be labeled with FRET probes, such as fluorescein, Cy5, Cy5.5, and BIODPY®.

The target nucleic acids captured and separated, which may further be detected by various procedures. In some embodiments, the target nucleic acids such as DNA may be detected by southern blot and RNA may be detected by northern blot. The target nucleic acids which are captured and separated at the capture zone, may be detected by colorimetric detection method, chemical, thermal, electrical, pH, luminescence or fluorescence based detection method.

In some embodiments, a primary detection probe is coupled to the target nucleic acid, the nucleic acid capture probe, or combinations thereof. As noted, the primary detection probe is "coupled" to the target nucleic acid or the nucleic acid capture probe, wherein the primary detection probe may be chemically or physically linked or attached to the target nucleic acid or the nucleic acid capture probe or both. In some embodiments, the target nucleic acid comprises a primary detection probe while present in the sample. In some other embodiments, the nucleic acid capture probe comprises a primary detection probe when immobilized on the substrate. In one embodiment, the primary detection probe is added to the sample before applied to the substrate, wherein the primary detection probe is coupled to the target nucleic acid. In some embodiments, the primary detection probe may be added to the nucleic acid capture probe on the substrate. The primary detection probe may be an antisense oligomer which hybridizes with the target nucleic acids, wherein the antisense oligomer probe can be detected. The detection probe may include but is not limited to, radioactive molecules, fluorescent molecules, proteins or peptides. For example, a radioactive isotope of phosphorus $^{32}P$ is inserted in the phosphodiester linkage of the antisense oligomer, which may function as a primary detection probe. The primary detection probe may be tagged with a non-radioactive marker, such as digoxygenin. In this case, anti-digoxygenin antibody may be used to detect the digoxygenin labelled probe. In some examples, the primary detection probe is a chemical entity, which in contact with a moiety attached to the target nucleic acids may generate fluorescence signal. The primary detection probe may be an enzyme, which on interaction with a moiety on the target nucleic acids may produce a chemical which generates a color. This may distinguish the colored target nucleic acid which is captured by the nucleic acid capture probe from the colorless template or non-target nucleic acids.

In some embodiments, the method further comprises: flowing a solution comprising primary detection probes through the sample application zone along the length of the substrate to bind to the captured target nucleic acid or captured target amplification product to form a primary detection probe bound target nucleic acid (or amplification product).

Some embodiments of the method further comprises: flowing a solution comprising a secondary detection probe through the sample application zone along the length of the substrate to bind to the primary detection probe, target nucleic acid or nucleic acid capture probe or combinations thereof. The secondary detection probe may bind to the primary detection probe bound target nucleic acid. In some embodiments, the primary detection probe may be attached to a fluorescence moiety, wherein the secondary detection probe may be selected as a quencher. The secondary detection probe may quench the fluorescence generated by the primary detection probe on interaction. In some other embodiments, the primary detection probe may be attached to a primary antibody, wherein the secondary detection probe may be selected as a secondary antibody, wherein the secondary antibody may bind to the primary antibody and generate a signal.

In some embodiments, after capture and separation of the target nucleic acids from the non-target nucleic acids or impurities, such as DNA and/or RNA, the target nucleic acids may be stabilized for extended storage, depending on its application and requirement. The target nucleic acid may be physically bound to the nucleic acid capture probe immobilized on the substrate, wherein the binding efficiency may be further increased using various reagents or conditions. In some embodiments, the stabilizing reagents may be impregnated in the substrate at the capture zone, which further stabilizes the captured target nucleic acid. In some embodiments, the stabilizing reagents may be impregnated at the sample application zone 14, capture zone 20 or in the entire substrate 12. The stabilization reagents are described in more detail in later part of the specification.

A liquid, such as a wash buffer, amplification reagents or amplification buffer flows along the length of the quartz fiber filter through the sample application zone and the migration of the target nucleic acid over the substrate depend on length of the nucleic acid. The target nucleic acid migrates on the quartz fiber filter, the lower the molecular weight, the further nucleic acid migrates on the quartz fiber filter from the sample application zone. In one or more embodiments of the method, a migration modifier is added to the substrate. The migration modifier modifies binding efficiency of the molecules to the substrate. In some embodiments, the sample application zone further comprises a migration modifier. The migration modifier may be used to modify the migration rate or pattern of the target nucleic acid using lateral flow. The migration modifier may decrease the migration rate of one or more template nucleic acid by ensuring better binding of the template nucleic acids to the substrate. Use of migration modifier ensures efficient capture, separation and detection of the target nucleic acid or amplified target nucleic acid.

In some embodiments, the migration modifier comprises a chaotrope. The migration modifier may comprise a guanidinium salt, which may minimize the migration of the template DNA during the lateral flow of the amplified product or target DNA. In one embodiment, the migration modifier comprises guanidinium thiocyanate. Generally, guanidinium thiocyanate improves binding of genomic DNA to the substrate, which retains the template nucleic acid, such as genomic DNA bound at the sample application zone.

In some embodiments, the method further comprises providing a wicking pad adjacent to the second end 31 of the substrate, which may function as a stopping pad or collection pad. The stopping pad may stop the flow of sample comprising nucleic acids near the second end. The stopping pad may be substituted by a flow barrier. The collection pad may collect the nucleic acids from the substrate by transferring the captured amplicons to the collection pad.

In some embodiments, the method further comprises adding a collection pad. In these embodiments, after diffusion of the washing buffer through the sample application zone 14 along the length of quartz fiber filter 12, the collection pad (a stopping pad, a wicking pad, or a quartz fiber filter) is disconnected from the substrate and replaced with a new collection pad so that the buffer flows from the substrate to the new collection pad.

In some embodiments, the substrate is a solid substrate, which is a non-water dissolvable material, which enables collection, extraction, separation, capture, detection and storage of nucleic acids followed by elution without solubilizing the material using water or aqueous buffer. In some embodiments, the substrate is an elongated strip comprising a first end 11, a sample application zone 14, and a second end 31. The run time starting from sample application to capture of target nucleic acid may increase with increasing the length of the target nucleic acid, as the high molecular weight target nucleic acid have low mobility and migrates slowly. The separation of the nucleic acids from the sample may be better with increasing the length of the substrate. The length of the substrate may be optimized considering better separation as well as run time. The substrate may have a length in a range between 1 cm and 20 cm. In some embodiments, the substrate has a length less than 10 cm.

The substrate includes, but is not limited to, materials such as cellulose, cellulose acetate, nitrocellulose, glass fibers or combinations thereof. In one embodiment, the substrate comprises cellulose. In one or more embodiments, the substrate is selected from a nitrocellulose membrane, a cellulose membrane, a cellulose acetate membrane, a regenerated cellulose membrane, a nitrocellulose mixed ester membranes, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, and any combination of two or more of the above membranes. In some embodiments, the substrate comprises modified cellulose, such as pegylated cellulose or pegylated nitro cellulose.

In some embodiments, the substrate is a porous substrate. In one embodiment, the substrate is a porous cellulose membrane. In one embodiment, the solid substrate is a porous cellulose paper, such as a cellulose substrate from GE Healthcare Life Sciences (formerly Whatman™). In one example, the cellulose substrate comprises 903-cellulose, FTA™ or FTA™ Elute.

The sample solution comprising nucleic acids is applied to the sample application zone 14 of the quartz fiber filter 12. The sample application zone 14 may be in any shape or configuration that the sample solution may be applied thereto. In some embodiments, the sample application zone 14 of the quartz fiber filter 12 comprises a lysis reagent and the biological sample comprising nucleic acids is directly applied to the sample application zone 14 of the quartz fiber filter 12. In one or more embodiments of the device, the sample application zone comprises an FTA pad.

In one or more embodiments, the substrate comprises one or more cell-lysis reagents, protein denaturing agents or stabilizing agents in a substantially dry state. In other embodiments, the substrate further comprises buffer reagents, reducing agents, and optionally free-radical scavengers in addition to protein denaturing agents in a dry state. The substrate may extract nucleic acids and preserve nucleic acids under dry conditions, wherein the dried nucleic acids may further be eluted from the substrate by re-hydrating with water or aqueous buffer.

As noted, the sample application zone comprises a lysis reagent, wherein the lysis reagent may comprise chaotropes. The examples of chaotropic substances include, but are not limited to, guanidinium hydrochloride, guanidinium chloride, guanidinium isothiocyanate/thiocyanate, sodium thiocyanate, sodium perchlorate, sodium iodide, potassium iodide, urea, and/or any combination thereof. A typical anionic chaotropic series, shown in order of decreasing chaotropic strength, includes: $CCl_3COO^-$, $CNS^-$, $CF_3COO^-$, $ClO_4^-$, $I^-$, $CH_3COO^-$, $Br^-$, $Cl^-$, or $CHO_2^-$. The lysis reagent may include chaotropic substances in concentrations of from 0.1 M to 10 M, or from 1 M to 10 M.

For some of the biological samples, such as bacteria, the lysis reagent may comprise, for example, lytic enzymes or the biological samples may be pretreated, for example, with lytic enzymes, prior to being lysed. The lysis reagent may also comprise protease, such as serine, cystine and metallic proteases. A protease free of nuclease may be used. A protease comprising a stabilizer, such as metallic ions, may be used. The protease may be used, upon addition, in an amount of preferably from about 0.001 IU to about 10 IU, more preferably from about 0.01 IU to about 1 IU, per ml of the whole lysis reagent.

In some embodiments, the lysis reagent also includes a sufficient amount of buffer. The examples of buffers for use in the lysis reagent include tris-(hydroxymethyl) aminomethane hydrochloride (Tris-HCl), sodium phosphate, sodium acetate, sodium tetraborate-boric acid and glycine-sodium hydroxide.

In some embodiments, the lysis reagent also includes a non-ionic surfactant, a cationic surfactant, an anionic surfactant, an amphoteric surfactant, and/or any combination thereof. Exemplary nonionic surfactants include, but are not limited to, t-octylphenoxypolyethoxyethanol (TRITON X-100™) (octylphenoxy)polyethoxyethanol (IGEPAL™ CA-630/NP-40), triethyleneglycol monolauryl ether (BRIJ™ 30), sorbitari monolaurate (SPAN™ 20), or the polysorbate family of chemicals, such as polysorbate 20 (i.e., TWEEN™ 20), TWEEN™ 40, TWEEN™ 60 and TWEEN™ 80 (Sigma-Aldrich, St. Louis, Mo.). Examples of cationic surfactants include cetyltrimethylammonium bromide, dodecyltrimethylammonium chloride, tetradecyltrimethylammonium chloride and cetylpyridinium chloride. The concentration of the surfactant in the lysis reagent could vary slightly among the different surfactants and depending on the components in the biological sample to be lysed. In some embodiments, the concentration of the surfactant is in a range of from about 0.01% to about 20% by weight. The lysis reagent may further comprise dithiothreitol (DTT).

In one embodiment, the substrate is impregnated with nucleic acid stabilizing reagents. These stabilizing reagents may include DNA-decomposing enzyme inhibitor, such as DNAse inhibitor and/or RNA-decomposing enzyme inhibitor, such as RNAse inhibitor, buffer reagents, or chelating agents (e.g., EDTA). As noted, the substrate comprises an RNase inhibitor, wherein the RNase inhibitor comprises vanadyl ribonucleoside complex (VRC), a nucleotide analogue, a commercially available RNase inhibitor (e.g., SUPERase-In™), or a triphosphate salts, such as sodium triphosphate. The substrate may comprise DNAse inhibitor, which may include but is not limited to, 2-mercaptoethanol, 2-nitro-5-thiocyanobenzoic acid, Actin, Alfatoxin B2a, G2, G2a, and M1, $Ca^{2+}$, EGTA, EDTA, Sodium dodecyl sulfate, Calf spleen inhibitor protein, Carbodiimide and cholesterol sulfate, Iodoacetate.

In some embodiments, the substrate comprises stabilizing reagent, which may include a reducing agent that facilitates denaturation of RNase and aids in the isolation of undegraded RNA. Exemplary reducing agent includes, but is not limited to, 2-aminoethanethiol, tris-carboxyethylphosphine (TCEP), and β-mercaptoethanol. As noted, the substrate further comprises a chelating agent, wherein the chelating agent is selected from ethylenediaminetetraacetic acid (EDTA), citric acid, ethylene glycol tetraacetic acid (EGTA) or combinations thereof.

The substrate may further comprise a UV protectant, a free-radical scavenger, a chelator or combinations thereof for stabilizing nucleic acids. Without intending to be limited to any specific UV protect, an exemplary antioxidants include, for example, hydroquinone monomethyl ether (MEHQ), hydroquinone (HQ), toluhydroquinone (THQ), uric acid, and ascorbic acid. In some embodiments, the antioxidant is THQ.

As noted, the non-target nucleic acid, residual lysis reagents, inhibitors or other impurities from the sample application zone 14 may be washed off from the substrate. The washing may be done before amplification of template nucleic acid and/or capture of the target nucleic acid using the amplification buffer. In some embodiments, an additional washing solution may be used, wherein the washing solution comprises an aqueous buffer, which may be any solvent of nucleic acids. In some embodiments, the aqueous buffer comprises tris(hydroxymethyl)aminomethane, ethylenediaminetetraacetic acid (EDTA) buffer, phosphate buffered saline (PBS) or Tris EDTA (TE) in which the tris buffer is substituted with HEPES. As noted, the aqueous buffer flows through the sample application zone 14 along the length of the substrate, such as quartz fiber filter 12. In some embodiments, the first end 11 of the substrate is placed into the aqueous buffer so that the aqueous buffer flows from the first end 11 of the substrate 12.

The washing buffer may comprise an enzyme capable of degrading a contaminant, e.g., protein. Moreover, it may comprise deoxyribonuclease, ribonuclease or the like depending on circumstances. Use of washing buffer comprising deoxyribonuclease allows selective recovery of RNA. Similarly, use of a ribonuclease-comprising washing buffer allows selective recovery of DNA.

The amplification buffer for washing the substrate may be applied to the quartz fiber filter at the same place as where the sample solution comprising nucleic acids is applied, i.e., the sample application zone. The amplification buffer may also be applied to the quartz fiber filter at a place different from both the sample application zone and the buffer loading portion.

In some embodiments, the amplification buffer flows to the second end 31 and carries unwanted contaminants in the sample solution to the second end. The second end 31 is then cut off before flowing the liquid to migrate the target nucleic acid or flowing the amplification reagents or amplification buffer. In such way, the target nucleic acids positioned on the capture zone 20 of the quartz fiber filter are separated/isolated from the unwanted contaminants. After diffusion of the liquid, such as an amplification buffer or wash buffer, the target nucleic acids positioned on the capture zone 20 of the quartz fiber filter 12 may be eluted under conditions of low ionic strength, high heat, electrophoresis, or other methods known in the art.

In some examples, the sample solution is absorbed, adsorbed or otherwise incorporated into or onto the sample application zone in such a way as not to be readily removed from the sample application zone unless subjected to conditions which are intentionally or inadvertently performed to remove the sorbed composition from the sample application zone.

The following examples are included to provide additional guidance to those of ordinary skill in the art in practicing the claimed invention. These examples do not limit the invention as defined in the appended claims.

EXAMPLES

Example 1: Preparation of GF/F Substrate

A GF/F porous matrix (Whatman®-GE Healthcare) was soaked in a solution of 280 mg/ml guanidinium thiocyanate (Sigma-Aldrich) and allowed to air dry. This treated matrix was then cut into 5×5 mm squares and each square assembled on a modified lateral flow strip using PDMS glue. Each lateral flow strip (substrate) 12 (FIG. 2) was modified by removing an area approximately 10-12 mm from the pointed tip 11 underneath where the 5 mm square of treated GF/F porous matrix 14 would reside. One strip was processed with a wick 28 present on the end opposite the point 11 (FIG. 2).

Example 2: Preparation of a Modified Porous Nitrocellulose Based Substrate

A modified porous matrix was prepared by soaking a nitrocellulose based substrate (GE Healthcare) in an aqueous solution containing 10% (w/v) polyethylene glycol methyl ether methacrylate 300 (PEG; Sigma-Aldrich) and 30% (v/v) Tween 20 (Sigma-Aldrich) for 10 seconds. Excess solution was removed and the treated matrix subjected to E-beam (Advanced Electron Beam) treatment for a total dose of 10 kGy. Following irradiation, the modified matrix was treated as follows: 1) washed by soaking three times for 30 minutes each in distilled water using an orbital rotating platform, 2) the excess water removed and 3) allowed to air dry at room temperature overnight.

Example 3: Preparation of RCA Amplicon (or RCA Capture Probe)

Rolling circle amplification reaction was performed to generate RCA product DNA. A 25 nucleotide (nt) long 5'-phosphorylated DNA oligonucleotide (oligo) probe with the sequence 5'-CATCATTGATTTAGACACTGAAAAA-3' (SEQ. ID No. 1) was annealed to a 20 nt scaffold oligo with the sequence 5'-ATCAATGATGTTTTTCAGTG-3' (SEQ. ID No. 2) and was circularized by ligating the ends to form a circularized template DNA. The sequences are present in Table 1 as reference.

TABLE 1

Sequences for oligonucleotides used for RCA reaction.

| Sample | SEQ. ID No. | Sequence |
|---|---|---|
| Oligonucleotide (oligo) probe | 1 | 5'-CATCATTGATTTAGACACTGAAAAA-3' |
| Scaffold oligo | 2 | 5'-ATCAATGATGTTTTTCAGTG-3' |

Annealing—The annealing reactions (40 µl) containing 10 mM Tris, pH 8.0, 50 mM NaCl, 100 pmol probe oligo, and 150 pmol scaffold oligo were incubated at 95° C. for 2 min and slowly cooled to 4° C. at a rate of 0.1° C. decrease of temperature per second.

Ligation—The ligation reactions (80 µl) containing 50 mM Tris, pH 7.5, 10 mM $MgCl_2$, 10 mM DTT, 1 mM ATP, 40 pmol annealed probe/scaffold oligo, and 1600 U T4 DNA ligase (NEB) were incubated at 23° C. for 16 hours, then incubated at 65° C. to inactivate the ligase.

Amplification—The circularized DNA template prepared as described above was amplified in two different RCA reactions, such as "high polymerase" and "low polymerase" RCA reactions. The circularized template DNA was amplified using a "high polymerase" rolling-circle amplification (RCA) reaction (270 µl) that contained 50 mM HEPES, pH 8.0, 20 mM $MgCl_2$, 0.01% Tween-20, 1 mM TCEP, 8.5 pmol circularized probe/scaffold oligo, 15 mM KCl, 400 µM dNTPs, and 5.4 µg Phi29 DNA polymerase. In another set, a "low polymerase" RCA reaction was performed; wherein the low polymerase RCA reaction was identical except that the quantity of Phi29 DNA polymerase was reduced to 0.6 µg. In the low polymerase amplification reactions, the reaction mixtures were incubated at 37° C. for 16 hours, further incubated at 65° C. for 20 min to heat-inactivate the polymerase, and then the amplified DNA was purified by ethanol precipitation and re-suspended in 250 µl of 10 mM Tris, pH 7.5, 0.1 mM EDTA.

Example 4: Preparation of Lactate Dehydrogenase I (LDH I) Amplicon

Different oligos used for amplification reaction with LDH are described in Table 2. 10 microliter of each of the reaction mixtures contained 1× reaction buffer (50 mM $KPO_4$ pH=7.6, 3.75 mM $MgSO_4$, 0.2 mM dNTP), 50 nM forward bumper primer and reverse bumper primers, 250 nM forward amplification primer, 500 nM reverse amplification primer, 6 units of N. BbvC1B restriction enzyme (purchased from New England Biolabs or NEB), 8 units of Bst2.0 warm start DNA polymerase (purchased from New England Biolabs or NEB), 200 nM biotinylated detection probe. The reaction mixtures further contained 1,000,000 copies of Methicillin-sensitive *Staphylococcus aureus* (MSSA) genomic DNA for test sample. Reactions were incubated at 50° C. for 30 minutes.

TABLE 2

Sequences for oligonucleotides used for LDH reaction

| Sample | SEQ. ID No. | Nucleic acid sequence |
|---|---|---|
| Forward Bumper Primer | 3 | 5'AGGTAATGGTGCAGTAGGT |
| Forward Amplification Primer | 4 | 5'GCATAATACTACCAGTCTCCTCAGCAAGC TACGCATTTTCATT |
| Reverse Amplification Primer | 5 | 5'TAGAATAGTCGCATACTTCCTCAGCACAT CTCCTCGAACTTTTT |
| Reverse Bumper Primer | 6 | 5'CCAGCTTTCACACGAAC |
| Biotinylated Detection Probe | 7 | 5'CTAATTCATCAACAATGC-biotin |

Example 5: Lateral Flow Assay Using RCA Capture Probe and Effect of Temperature RCA products prepared from reactions with either low polymerase concentrations (0.6 micrograms/reaction) or high polymerase concentrations (5.4 micrograms/reaction) were spotted onto nitrocellulose membranes (NC) or modified nitrocellulose membranes with PEG (NC-PEG) using a pipette, at a concentration of 9 pmol per $mm^2$, followed by drying overnight under ambient conditions. The RCA product applied and dried on the NC or NC-PEG substrate was used as nucleic acid capture probe and the line of RCA probe application was at one end of the lateral flow substrate, may be referred to herein as test line. For control experiments, nucleic acid probe was attached to the substrate by cross-linking and used as a nucleic acid capture probe.

The nitrocellulose (NC) or modified nitrocellulose (NC-PEG) membranes loaded with RCA capture probe (width 5 mm and length 4 cm) and the cellulose membrane (length 12 mm) were then assembled to form a lateral flow device (LFDs). In the LFD (or lateral flow strip), the cellulose absorbent pad was disposed on the nitrocellulose (NC) or modified nitrocellulose (NC-PEG) membrane near one end of the NC or NC-PEG membrane, such that 2 mm cellulose pad was in contact (overlap) with the nitrocellulose or modified nitrocellulose membrane.

Lateral flow assays were performed by dipping one end of the LFD into a 100-μl running buffer. The running buffer contains: 1) 10 μl lactate dehydrogenase I (LDH I) amplicons generated by isothermal strand displacement amplification (iSDA) reaction at the input of $10^6$ Methicillin-sensitive *Staphylococcus aureus* (MSSA) genomic DNA; 2) 10 μg of 300 μm blue bead (from Seradyn) functionalized with streptavidin; and 3) 15 mM HEPES at pH 6.8, 2.5 mg/ml BSA, and 1% Triton X-100. The assay temperature was either at room temperature or at 50° C. The effect of additional 0.4 M NaCl on test line hybridization was also tested at 50° C. For test lateral flow device or strips, RCA DNA capture probed substrate was dipped in the running buffer.

The lateral flow assays were performed at room temperature and at 50° C. for low polymerase and high polymerase concentration and the results are demonstrated in FIGS. 4 A and 4B, respectively. The detection performance at room temperature and at 50° C. were determined, wherein the intensity of the bands (test line) for RCA capture probe on the substrate after capturing the target nucleic acid at different temperatures remain same for low polymerase (left panel) and high polymerase (right panel) concentration, as shown in the FIGS. 4 A, 4B respectively. The results (FIGS. 4 A, 4B) demonstrate that the RCA capture probe did not migrate laterally during flow, despite the fact that the RCA capture probe was not cross-linked or otherwise attached to the substrate. Due to low molecular weight, the target nucleic acid or target amplicon (generated by iSDA) migrated through the matrix, and was captured by hybridization to the RCA capture probe which was immobilized on the substrate due to its high molecular weight. Due to increased capture length, the efficiency of binding of the target nucleic acid to the RCA capture probe is high. Further, the high melting temperature of RCA capture probe ensures the stability of the RCA nucleic acid at higher temperature (50° C.) and provide high capture efficiency (FIG. 4B), in contrast to other nucleic acid capture probes which are unstable at 50° C. The low molecular weight capture probe required UV-induced crosslinking to attach to one location of the substrate during lateral flow (data not shown). By utilizing a high molecular weight RCA capture probe which cannot migrate laterally during flow, the step of crosslinking the capture probe to the matrix was obviated. Further, by adding 0.4M NaCl salt to both of the capture probes (RCA and low molecular weight nucleic acid), the band intensity of the RCA DNA capture probe almost remained same both at low and high temperature. There was no obvious effect of salt concentration on capture as well as detection efficiency of RCA capture probe.

Example 6: Effect of RCA Capture Probe Concentration on Lateral Flow Assay

In order to investigate the effect of concentration of RCA capture probe on the sensitivity of the lateral flow assay, different concentration of RCA capture probes (2.3, 9, or 45 pmol per 5 $mm^2$) were applied on the NC-PEG substrate and dried for one day. The NC-PEG membranes were then assembled into lateral flow devices (LFDs) as mentioned above. Lateral flow assays were performed by dipping one end of the LFD into a 100-μl running buffer which contains: 10 μl LDH1 amplicons generated by isothermal strand displacement amplification (iSDA) reaction at the input of $10^6$ genomic MSSA DNA; 10 μg of 300 μm blue bead (from Seradyn) functionalized with streptavidin; and 15 mM HEPES at pH 6.8, 2.5 mg/ml BSA, and 1% Triton X-100. The assays were performed either at room temperature or at 50° C., and the signal intensity on each lateral flow strip was quantified by subtracting the background signal from the intensity of the 1-mm front of RCA bands using Image J (NIH software). As a note, the typical test line width in a lateral flow test is considered as 1 mm.

The signal generated on the captured nucleic acid within minutes after the lateral flow assay under room temperature. The assay was over in 30 minutes, and the images of the lateral flow assay strips were quantified using Image J software. As shown in FIGS. 5A and 5B, the signal intensity of the band increased with increased concentration of the RCA capture probe on the NC-PEG membrane under room temperature and at 50° C. The signal intensities of the RCA capture probe were quantified at low and high temperature for different concentrations from FIGS. 5A and 5B using Image J software, as shown in FIG. 5C. This result demonstrates that despite being entangled on the substrate, the functionality of the high molecular weight RCA capture probe which was not cross-linked or attached to the substrate has high capture efficiency. The result also ruled out the possibility of poor binding ability of the high molecular weight RCA capture probe due to structural hindrance for entanglement of the probe within the substrate.

Example 7: Effect of Substrate and Drying Condition on Different Concentration of Capture Probes in Lateral Flow Assay The RCA probe was produced at a larger volume and was dispensed onto NC-PEG membrane or unmodified nitrocellulose (GEHC FF80HP) membrane as a test line (T) using BioDot XYZ-3000 dispensing platform. BSA-Biotin was also dispensed on the membranes as a control line (C) which captures any reporting particles that flows through the membrane. After drying the membranes loaded with RCA probes, the membranes were then assembled into lateral flow devices (LFDs) as described above. The final concentrations of RCA probe on the membrane were 2.3, 9, or 22.5 pmol per test line (1 mm×5 mm) After drying of RCA probe on the membranes for either one (1) day or two (2) days, the lateral flow assays were performed by dipping one end of the LFD into a 100-μl running buffer. The running buffer contains: 10 μl LDH1 amplicons generated by isothermal strand displacement amplification (iSDA) reaction at the input of $10^6$ genomic MSSA DNA; 1 OD of 40 nm gold particles covalently functionalized with streptavidin (Innova Biosciences); and PBS at pH 7.4.

As shown in the FIGS. 6A and 6B, signal intensity of test line is a function of probe concentration, when the target nucleic acid (amplicon) concentration is constant. The signal intensity at day 2 is generally higher than day 1 on NC-PEG membrane, and similar performance were observed for NC-PEG and unmodified FF80HP nitrocellulose membranes at day 2 (after RCA was completely physically absorbed onto the membrane surfaces).

Example 8: Determination of Sensitivity of Lateral Flow Detection for Amplicons

This example was performed to determine sensitivity of lateral flow detection for RCA capture probe. When the input of template nucleic acid is less, generally the efficiency of amplicon production is also decreased which results in less signal intensity in lateral flow assay (LFA). In this experiment, the RCA probe concentration was 67 pmol per test line (1 mm×5 mm) and loaded on a NC-PEG membrane of a lateral flow assay strip. Lateral flow assays were run using target amplicon (target nucleic acid) derived from isothermal DNA amplification (iSDA) reactions, wherein the input template nucleic acid concentration was different, such as $10^2$ and $10^6$ number of cells comprising MSSA genomic DNA. The cells were lysed and applied to the amplification reaction mixture as a source of template nucleic acid. As shown in FIG. 7, there is no test line signal development for "no template control" (NTC) sample (lane 1) which does not contain genomic DNA in the iSDA reaction. It was possible to detect target amplicon (lanes 2, 3, 4) using the RCA probe applied to the lateral flow detection strips, wherein the target amplicons were derived from iSDA reactions wherein the MSSA genomic DNA was derived from $10^2$ cells (lanes 2, 3, 4) and $10^6$ cells (5, 6, 7) at either room temperature with different drying conditions of RCA probes (day 1 and day 5) and at 50° C. There was a broad range of detection limit for RCA probes as shown the strong signal intensity when the concentration of MSSA genomic DNA was increased from $10^2$ to $10^6$ as shown in FIG. 7. This result again demonstrated that the RCA capture probe remain in one location during lateral flow, without crosslinking or any other immobilization as required for low molecular weight capture probes. Further, despite the entanglement of the RCA capture probe on the substrate, the RCA capture probe has excellent sensitivity for detection.

While the disclosure has been illustrated and described in typical embodiments, it is not intended to be limited to the details shown, since various modifications and substitutions may be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method of capturing a target nucleic acid on a capture zone of a substrate, comprising:
applying a nucleic acid capture probe to a capture zone of a substrate, wherein the nucleic acid capture probe has a first molecular weight and comprises multiple copies of an identical region that is complementary to at least a portion of a sequence of the target nucleic acid such that the target nucleic acid hybridizes to multiple regions of the nucleic acid capture probe after the target nucleic acid interacts with the nucleic acid capture probe on the capture zone of the substrate, wherein the nucleic acid capture probe is a rolling circle amplification (RCA) product and has a length in a range from about 20,000 bases to about 150,000 bases, wherein the nucleic acid capture probe is substantially immobilized at the capture zone of the substrate by entanglement of the nucleic acid capture probe with the substrate;
thereafter applying a sample comprising the target nucleic acid to a sample application zone of the substrate and flowing the sample comprising the target nucleic acid across a length of the substrate from the sample application zone to the capture zone by a lateral flow, wherein the target nucleic acid has a second molecular weight; and
capturing the target nucleic acid using the nucleic acid capture probe by hybridization of the target nucleic acid to the nucleic acid capture probe on the capture zone of the substrate.

2. The method of claim 1, further comprising flowing a liquid across the length of the substrate from the sample application zone to the capture zone to migrate the target nucleic acid from the sample application zone to the capture zone by the lateral flow.

3. The method of claim 2, wherein the sample further comprises a template nucleic acid having a third molecular weight and the liquid is a nucleic acid amplification reaction mixture that amplifies the template nucleic acid to form a target nucleic acid amplification product.

4. The method of claim 1, wherein the nucleic acid capture probe comprises multiple tandem repeat sequences.

5. The method of claim 1, wherein the nucleic acid capture probe comprises 20 to 150 nucleotides of tandem repeat sequences.

6. The method of claim 1, wherein the nucleic acid capture probe comprises a single stranded nucleic acid.

7. The method of claim 1, wherein the nucleic acid capture probe comprises deoxyribonucleic acid (DNA), ribonucleic acid (RNA), nucleotide analogues, or combinations thereof.

8. The method of claim 1, further comprising contacting the sample with a lysis reagent.

9. The method of claim 8, wherein the lysis reagent is impregnated in the sample application zone.

10. The method of claim 1, wherein the sample comprises a lysis reagent.

11. The method of claim 1, wherein the sample application zone further comprises a migration modifier.

12. The method of claim 11, wherein the migration modifier comprises a chaotrope.

13. The method of claim 11, wherein the migration modifier comprises guanidinium thiocyanate.

14. The method of claim 1, wherein the sample further comprises one or more inhibitors, a non-target nucleic acid, lysis reagents, or combinations thereof, and wherein the method further comprises washing the substrate to remove one or more of the inhibitors, the non-target nucleic acid, the lysis reagents, or the combinations thereof present on the substrate.

15. The method of claim 1, wherein a primary detection probe is added to the target nucleic acid at the sample application zone of the substrate, or the primary detection probe is added to the nucleic acid capture probe at the capture zone of the substrate, or the primary detection probe is added to both the target nucleic acid at the sample application zone of the substrate and to the nucleic acid capture probe at the capture zone of the substrate.

16. The method of claim 1, wherein the target nucleic acid or the nucleic acid capture probe or both the target nucleic acid and the nucleic acid capture probe further comprises a primary detection probe.

17. The method of claim 16, wherein the primary detection probe comprises a chromophore moiety, a fluorescent moiety, a phosphorescence moiety, an affinity probe, a magnetic probe, a paramagnetic probe, a metallic probe, or combinations thereof.

18. The method of claim 16, wherein the primary detection probe comprises a binding moiety selected from an antibody, a biotin, a streptavidin bead, a gold particle, or combinations thereof.

19. The method of claim 16, further comprising flowing a solution comprising a secondary detection probe from the sample application zone along the length of the substrate to the capture zone, wherein the secondary detection probe binds to the primary detection probe of the target nucleic acid, or to the primary detection probe of the nucleic acid capture probe, or to both the primary detection probe of the target nucleic acid and the primary detection probe of the nucleic acid capture probe.

20. The method of claim 1, wherein the substrate is an elongated strip comprising a first end, a sample application zone, a capture zone, and a second end.

21. The method of claim 20, wherein the substrate further comprises a wicking pad disposed adjacent to the second end.

22. The method of claim 20, wherein the substrate further comprises a stopping pad disposed adjacent to the second end.

23. The method of claim 1, wherein the substrate comprises a cellulose membrane, a nitrocellulose membrane, modified porous nitrocellulose or cellulose based substrates, polyethyleneglycol-modified nitrocellulose, a cellulose acetate membrane, a nitrocellulose mixed ester membrane, a glass fiber, a quartz fiber, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, or combinations thereof.

24. The method of claim 1, wherein the nucleic acid capture probe has a length of 120,000 bases.

25. A method of capturing a target nucleic acid on a capture zone of a substrate, comprising:
applying a nucleic acid capture probe to a capture zone of a substrate, wherein the nucleic acid capture probe has a first molecular weight and comprises multiple copies of an identical region that is complementary to at least a portion of a sequence of the target nucleic acid such that the target nucleic acid hybridizes to multiple regions of the nucleic acid capture probe after the target nucleic acid interacts with the nucleic acid capture probe on the capture zone of the substrate, wherein the nucleic acid capture probe has a length in a range from about 20,000 bases to 150,000 bases, and wherein the nucleic acid capture probe is substantially immobilized at the capture zone of the substrate by entanglement of the nucleic acid capture probe with the substrate at the capture zone;
thereafter applying a sample comprising the target nucleic acid to a sample application zone of the substrate, wherein the target nucleic acid has a second molecular weight;
flowing a liquid across a length of the substrate from the sample application zone to the capture zone to migrate the target nucleic acid from the sample application zone to the capture zone by a lateral flow; and
capturing the target nucleic acid using the nucleic acid capture probe by hybridization of the target nucleic acid to the nucleic acid capture probe on the capture zone of the substrate.

26. The method of claim 25, wherein the nucleic acid capture probe has a length of 120,000 bases.

* * * * *

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
catcattgat ttagacactg aaaaa                                              25

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
atcaatgatg tttttcagtg                                                   20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
```
aggtaatggt gcagtaggt                                                  19

<210> SEQ ID NO 4
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcataatact accagtctcc tcagcaagct acgcattttc att                       43

<210> SEQ ID NO 5
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tagaatagtc gcatacttcc tcagcacatc tcctcgaact tttt                      44

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccagctttca cacgaac                                                    17

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' Biotin

<400> SEQUENCE: 7
ctaattcatc aacaatgc                                                   18

<210> SEQ ID NO 8
<211> LENGTH: 103
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
ctcagcaagc tacgcatttt cattagtgaa ccaaagcatt gttgatgaat tagtcatcat     60
tgatttagac actgaaaaag ttcgaggaga tgttatggct gag                      103

<210> SEQ ID NO 9
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 9
tttttcagtg tctaaatcaa tgatgttttt cagtgtctaa atcaatgatg tttttcagtg        60
tctaaatcaa tgatgttttt cagtgtctaa atcaatgatg tttttcagtg tctaaatcaa       120
tgatgttttt cagtgtctaa atcaatgatg                                        150
```